(12) United States Patent
Colton et al.

(10) Patent No.: US 10,179,901 B2
(45) Date of Patent: Jan. 15, 2019

(54) METHODS AND COMPOSITIONS FOR INCREASED SAFETY OF STEM CELL-DERIVED POPULATIONS

(71) Applicant: Massachusetts Institute of Technology, Cambridge, MA (US)

(72) Inventors: Clark K. Colton, Newton, MA (US); Jeffrey R. Millman, St. Louis, MO (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/179,175

(22) Filed: Jun. 10, 2016

(65) Prior Publication Data

US 2017/0121677 A1 May 4, 2017

Related U.S. Application Data

(62) Division of application No. 13/382,965, filed as application No. PCT/US2010/001934 on Jul. 9, 2010, now Pat. No. 9,388,381.

(60) Provisional application No. 61/251,048, filed on Oct. 13, 2009, provisional application No. 61/224,225, filed on Jul. 9, 2009.

(51) Int. Cl.
*C12N 5/0735* (2010.01)
*C12N 5/074* (2010.01)

(52) U.S. Cl.
CPC ......... *C12N 5/0606* (2013.01); *C12N 5/0696* (2013.01); *C12N 2500/02* (2013.01)

(58) Field of Classification Search
None
See application file for complete search history.

(56) References Cited

U.S. PATENT DOCUMENTS

| | | | |
|---|---|---|---|
| 5,134,057 A | 7/1992 | Kuypers et al. | |
| 5,314,960 A | 5/1994 | Spinelli et al. | |
| 5,459,069 A * | 10/1995 | Palsson ............... | C07K 14/535 435/289.1 |
| 5,942,435 A | 8/1999 | Wheeler | |
| 6,534,052 B1 | 3/2003 | Xiao et al. | |
| 6,613,568 B2 | 9/2003 | Kaufman et al. | |
| 6,833,269 B2 | 12/2004 | Carpenter | |
| 7,033,831 B2 | 4/2006 | Fisk et al. | |
| 7,250,294 B2 | 7/2007 | Carpenter et al. | |
| 7,282,366 B2 | 10/2007 | Rambhatle et al. | |
| 7,326,572 B2 | 2/2008 | Fisk et al. | |
| 7,425,448 B2 | 9/2008 | Xu | |
| 7,732,199 B2 | 6/2010 | Xu | |
| 7,763,464 B2 | 7/2010 | Xu | |
| 9,029,147 B2 | 5/2015 | Colton et al. | |
| 9,388,381 B2 | 7/2016 | Colton et al. | |
| 9,447,378 B2 | 9/2016 | Colton et al. | |
| 9,816,070 B2 | 11/2017 | Colton et al. | |
| 2002/0120084 A1 | 8/2002 | Valint et al. | |
| 2005/0164382 A1 | 7/2005 | Xu | |
| 2005/0266554 A1 | 12/2005 | D'Amour et al. | |
| 2007/0259421 A1 | 11/2007 | D'Amour et al. | |
| 2010/0261277 A1 | 10/2010 | Colton et al. | |
| 2011/0312087 A1 | 12/2011 | Khan | |
| 2012/0219532 A1 | 8/2012 | Colton et al. | |
| 2013/0287743 A1 | 10/2013 | Colton et al. | |
| 2014/0370598 A1 | 6/2014 | Colton et al. | |

FOREIGN PATENT DOCUMENTS

| | | | |
|---|---|---|---|
| WO | WO 2000/29550 A2 | 5/2000 | |
| WO | WO-2008156708 A2 * | 12/2008 | ........... C12N 5/0657 |
| WO | WO 2009/007852 A2 | 1/2009 | |
| WO | WO 2009/035217 A1 | 3/2009 | |
| WO | WO 2009/079007 A1 | 6/2009 | |
| WO | WO 2011/005326 A1 | 1/2011 | |

OTHER PUBLICATIONS

Dang, Stephen M; et al; "Controlled, Scalable Embryonic Stem Cell Differentiation Culture" Stem Cells, 22, 275-282, 2004 (Year: 2004).*
Simon, M. Celeste; Keith, Brian; "The role of oxygen availability in embryonic development and stem cell function" Molecular Cell Biology, 9, 285-296, 2008 (Year: 2008).*
[No Author Listed] FDA Center for Biologics Evaluation and Research: Cellular, Tissue, and Gene Therapeutics Advisory Committee, Summary Minutes. Meeting #45. Apr. 10-11, 2008.
[No Author Listed]. Innovative cell culture device to help expand your growth. Wilson Wolf Manufacturing, Inc. Accessed online at http://www.wilsonwolf.com/technology.htm on Jun. 4, 2008. 1 page.
Ai et al., Biocompatibility of layer-by-layer self-assembled nanofilm on silicone rubber for neurons. J Neurosci Methods. Sep. 30, 2003;128(1-2):1-8.
Avgoustiniatos, Oxygen diffusion limitations in pancreatic islet culture and immunoisolation. Thesis; Massachusetts Institute of Technology.2002.
Baharvand et al., Differentiation of human embryonic stem cells into hepatocytes in 2D and 3D culture systems in vitro. Int J Dev Biol. 2006;50(7):645-52.
Bauwens et al., Development of a perfusion fed bioreactor for embryonic stem cell-derived cardiomyocyte generation: oxygen-mediated enhancement of cardiomyocyte output. Biotechnol Bioeng. May 20, 2005;90(4):452-61.
Bjorklund et al., Embryonic stem cells develop into functional dopaminergic neurons after transplantation in a Parkinson rat model. Proc Natl Acad Sci U S A. Feb. 19, 2002;99(4):2344-9. Epub Jan. 8, 2002.

(Continued)

*Primary Examiner* — David W Berke-Schlessel
(74) *Attorney, Agent, or Firm* — Wolf, Greenfield & Sacks, P.C.

(57) ABSTRACT

The invention provides methods and compositions relating to differentiated cell populations that derive from pluripotent stem cells. The methods relate to reducing the number of residual stem cells present in such populations. The compositions include differentiated cell populations that contain reduced number of stem cells or that contain no stem cells. Pluripotent stem cells may be reduced in number and/or function through exposure to low oxygen levels.

17 Claims, 21 Drawing Sheets

Specification includes a Sequence Listing.

(56) References Cited

OTHER PUBLICATIONS

Blum et al., Clonal analysis of human embryonic stem cell differentiation into teratomas. Stem Cells. Aug. 2007;25(8):1924-30. Epub Apr. 26, 2007.
Blum et al., The tumorigenicity of human embryonic stem cells. Adv Cancer Res. 2008;100:133-58.
Bondue et al., Mesp1 acts as a master regulator of multipotent cardiovascular progenitor specification. Cell Stem Cell. Jul. 3, 2008;3(1):69-84.
Bonner-Weir et al., In vitro cultivation of human islets from expanded ductal tissue. Proc Natl Acad Sci U S A. Jul. 5, 2000;97(14):7999-8004.
Brederlau et al., Transplantation of human embryonic stem cell-derived cells to a rat model of Parkinson's disease: effect of in vitro differentiation on graft survival and teratoma formation. Stem Cells. Jun. 2006;24(6):1433-40. Epub Mar. 23, 2006.
Brunelle et al., Oxygen deprivation induced cell death: an update. Apoptosis. Dec. 2002;7(6):475-82.
Brusselmans et al., A novel role for vascular endothelial growth factor as an autocrine survival factor for embryonic stem cells during hypoxia. J Biol Chem. Feb. 4, 2005;280(5):3493-9. Epub Nov. 29, 2004.
Caspi et al., Transplantation of human embryonic stem cell-derived cardiomyocytes improves myocardial performance in infarcted rat hearts. J Am Coll Cardiol. Nov. 6, 2007;50(19):1884-93. Epub Oct. 23, 2007.
Csete, Oxygen in the cultivation of stem cells. Ann N Y Acad Sci. May 2005;1049:1-8.
Cunningham et al., Quantification of fibronectin adsorption to silicone-rubber cell culture substrates. Biotechniques.Apr. 2002;32(4):876, 878, 880 passim.
Daley et al., Realistic prospects for stem cell therapeutics. Hematology Am Soc Hematol Educ Program. 2003:398-418.
Damjanov et al., The terminology of teratocarcinomas and teratomas. Nat Biotechnol. Nov. 2007;25(11):1212; discussion 1212.
D'Amour et al., Efficient differentiation of human embryonic stem cells to definitive endoderm. Nat Biotechnol. Dec. 2005;23(12):1534-41. Epub Oct. 28, 2005.
D'Amour et al., Production of pancreatic hormone-expressing endocrine cells from human embryonic stem cells. Nat Biotechnol. Nov. 2006;24(11):1392-401. Epub Oct. 19, 2006.
David et al., MesP1 drives vertebrate cardiovascular differentiation through Dkk-1-mediated blockade of Wnt-signalling. Nat Cell Biol. Mar. 2008;10(3):338-45. Epub Feb. 24, 2008. Supplementary Information.
Drukker et al., Human embryonic stem cells and their differentiated derivatives are less susceptible to immune rejection than adult cells. Stem Cells. Feb. 2006;24(2):221-9. Epub Aug. 18, 2005.
Erdö et al., Host-dependent tumorigenesis of embryonic stem cell transplantation in experimental stroke. J Cereb Blood Flow Metab. Jul. 2003;23(7):780-5.
Fehling et al., Tracking mesoderm induction and its specification to the hemangioblast during embryonic stem cell differentiation. Development. Sep. 2003;130(17):4217-27.
Fernandes et al., Different stages of pluripotency determine distinct patterns of proliferation, metabolism, and lineage commitment of embryonic stem cells under hypoxia. Stem Cell Res. Jul. 2010;5(1):76-89. Epub Apr. 22, 2010.
Fraker et al., Enhanced oxygenation promotes beta-cell differentiation in vitro. Stem Cells. Dec. 2007;25(12):3155-64. Epub Aug. 30, 2007.
Fukuda et al., Stem cells as a source of regenerative cardiomyocytes. Circ Res. Apr. 28, 2006;98(8):1002-13.
Gerecht-Nir et al., Human embryonic stem cells as an in vitro model for human vascular development and the induction of vascular differentiation. Lab Invest. Dec. 2003;83(12):1811-20.
Ginis et al., Differences between human and mouse embryonic stem cells. Dev Biol. May 15, 2004;269(2):360-80.
Grapin-Botton et al., Endoderm development: from patterning to organogenesis. Trends Genet. Mar. 2000;16(3):124-30.
Gu et al., Direct lineage tracing reveals the ontogeny of pancreatic cell fates during mouse embryogenesis. Mech Dev. Jan. 2003;120(1):35-43.
Hentze et al., Cell therapy and the safety of embryonic stem cell-derived grafts. Trends Biotechnol. Jan. 2007;25(1):24-32. Epub Nov. 3, 2006.
Hoffman et al., Characterization and culture of human embryonic stem cells. Nat Biotechnol. Jun. 2005;23(6):699-708.
Horton et al., Engineering microenvironments for embryonic stem cell differentiation to cardiomyocytes. Regen Med. Sep. 2009;4(5):721-32.
Humphrey et al., Maintenance of pluripotency in human embryonic stem cells is STAT3 independent. Stem Cells. 2004;22(4):522-30.
Jaenisch et al., Stem cells, the molecular circuitry of pluripotency and nuclear reprogramming. Cell. Feb. 22, 2008;132(4):567-82.
Jensen et al., Diffusion in tissue cultures on gas-permeable and impermeable supports. J Theor Biol. Feb. 1976;56(2):443-58.
Kaufman et al., Hematopoietic colony-forming cells derived from human embryonic stem cells. Proc Natl Acad Sci USA. Sep. 11, 2001;98(19):10716-21. Epub Sep. 4, 2001.
Kehat et al., Human embryonic stem cells for myocardial regeneration. Heart Fail Rev. Jul. 2003;8(3):229-36.
Keller. Embryonic stem cell differentiation: emergence of a new era in biology and medicine. Genes Dev. May 15, 2005;19(10):1129-55.
Kim et al., Dopamine neurons derived from embryonic stem cells function in an animal model of Parkinson's disease. Nature. Jul. 4, 2002;418(6893):50-6. Epub Jun. 20, 2002.
Kim et al., Increase in dopaminergic neurons from mouse embryonic stem cell-derived neural progenitor/stem cells is mediated by hypoxia inducible factor-1alpha. J Neurosci Res. Aug. 15, 2008;86(11):2353-62.
Klug et al., Genetically selected cardiomyocytes from differentiating embronic stem cells form stable intracardiac grafts. J Clin Invest. Jul. 1, 1996;98(1):216-24.
Koay et al., Hypoxic chondrogenic differentiation of human embryonic stem cells enhances cartilage protein synthesis and biomechanical functionality. Osteoarthritis Cartilage. Dec. 2008;16(12):1450-6. Epub Jun. 9, 2008.
Kroon et al., Pancreatic endoderm derived from human embryonic stem cells generates glucose-responsive insulin-secreting cells in vivo. Nat Biotechnol. Apr. 2008;26(4):443-52. Epub Feb. 20, 2008.
Kurosawa et al., Effect of oxygen on in vitro differentiation of mouse embryonic stem cells. J Biosci Bioeng. Jan. 2006;101(1):26-30.
Laflamme et al., Cardiomyocytes derived from human embryonic stem cells in pro-survival factors enhance function of infarcted rat hearts. Nat Biotechnol. Sep. 2007;25(9):1015-24. Epub Aug. 26, 2007.
Lam et al., Multipotent progenitor cells in regenerative cardiovascular medicine. Pediatr Cardiol. Jul. 2009;30(5):690-8. Epub May 5, 2009.
Lavon et al., Differentiation and isolation of hepatic-like cells from human embryonic stem cells. Differentiation. Jun. 2004;72(5):230-8.
Lawrenz et al., Highly sensitive biosafety model for stem-cell-derived grafts. Cytotherapy. 2004;6(3):212-22.
Lee et al., Efficient generation of midbrain and hindbrain neurons from mouse embryonic stem cells. Nat Biotechnol. Jun. 2000;18(6):675-9.
Lensch et al., The terminology of teratocarcinomas and teratomas. Nat Biotechnol. Nov. 2007;25(11):1211; author reply 1211-2.
Leor et al., Human embryonic stem cell transplantation to repair the infarcted myocardium. Heart. Oct. 2007;93(10):1278-84. Epub Jun. 12, 2007.
Lindsley et al., Mesp1 coordinately regulates cardiovascular fate restriction and epithelial-mesenchymal transition in differentiating ESCs. Cell Stem Cell. Jul. 3, 2008;3(1):55-68.
Ma et al., Hypoxia and stem cell-based engineering of mesenchymal tissues. Biotechnol Prog. Jan.-Feb. 2009;25(1):32-42.

(56) References Cited

OTHER PUBLICATIONS

McLimans et al., Kinetics of gas diffusion in mammalian cell culture systems. I. Experimental. Biotechnol Bioeng. Nov. 1968;10:725-740.

Millman et al. "Extended Low Oxygen Culture of Mouse Embryonic Stem Cells Reduces the Fraction of Tumor-Forming Residual Pluripotent Cells in Differentiated Populations", NIH Symposium on Cardiovascular Regenerative Medicine, Bethesda, MD, Oct. 14-15, 2009.

Millman et al., "Differentiation of murine embryonic stem cells under low oxygen influences cardiomyocyte yield and timing and magnitude of cardiomyocyte gene expression", NIH Symposium on Cardiovascular Regenerative Medicine, Bethesda, MD, Oct. 14-15, 2009.

Millman et al., Culture under low oxygen conditions markedly enhances differentiation of murine embryonic stem cells into cardiomyocytes, The 5$^{th}$ International Society for Stem Cell Research (ISSCR) Annual Meeting, Cairns, Australia, Jun. 17-20, 2007.

Millman et al., Low oxygen influences the self-renewal and differentiation of murine embryonic stem cells, The 6$^{th}$ International Society for Stem Cell Research (ISSCR) Annual Meeting, Philadelphia, PA, Jun. 11-14, 2008.

Millman et al., The effects of low oxygen on self-renewal and differentiation of embryonic stem cells. Curr Opin Organ Transplant. Dec. 2009;14(6):694-700.

Mondragon-Teran et al., Lowering oxygen tension enhances the differentiation of mouse embryonic stem cells into neuronal cells. Biotechnol Prog. Sep.-Oct. 2009;25(5):1480-8.

Monge, Improvement of silicone endothelialization by treatment with allylamine and/or acrylic acid low-pressure plasma. J Appl. Polymer. Mar. 14, 2003;87(11):1794-1802.

Niebruegge et al., Generation of human embryonic stem cell-derived mesoderm and cardiac cells using size-specified aggregates in an oxygen-controlled bioreactor. Biotechnol Bioeng. Feb. 1, 2009;102(2):493-507.

Nir et al., Human embryonic stem cells for cardiovascular repair. Cardiovasc Res. May 1, 2003;58(2):313-23.

Okazaki et al., Oxygen, epigenetics and stem cell fate. Regen Med. Jan. 2006;1(1):71-83.

Papas et al., High-density culture of human islets on top of silicone rubber membranes. Transplant Proc. Oct. 2005;37(8):3412-4.

Pei, Regulation of pluripotency and reprogramming by transcription factors. J Biol Chem. Feb. 6, 2009;284(6):3365-9. Epub Sep. 26, 2008.

Pera et al., Regulation of human embryonic stem cell differentiation by BMP-2 and its antagonist noggin. J Cell Sci. Mar. 1, 2004;117(Pt 7):1269-80.

Powers et al., Accurate control of oxygen level in cells during culture on silicone rubber membranes with application to stem cell differentiation. Biotechnol Prog. May-Jun. 2010;26(3):805-18.

Powers et al., Effects of oxygen on mouse embryonic stem cell growth, phenotype retention, and cellular energetics. Biotechnol Bioeng. Oct. 1, 2008;101(2):241-54.

Przyborski, Differentiation of human embryonic stem cells after transplantation in immune-deficient mice. Stem Cells. Oct. 2005;23(9):1242-50.

Purpura et al., Soluble Flt-1 regulates Flk-1 activation to control hematopoietic and endothelial development in an oxygen-responsive manner. Stem Cells. Nov. 2008;26(11):2832-42. Epub Sep. 4, 2008.

Rambhatla et al., Generation of hepatocyte-like cells from human embryonic stem cells. Cell Transplant. 2003;12(1):1-11.

Ramirez et al., Effect of Oxygen tension and substrate on growth and differentiation of mouse embryonic stem cells. Reprod Fertil Dev. 2006;18(2):209-10.

Ramírez-Bergeron et al., Hypoxia affects mesoderm and enhances hemangioblast specification during early development. Development. Sep. 2004;131(18):4623-34.

Ramírez-Bergeron et al., Hypoxia-inducible factor and the development of stem cells of the cardiovascular system. Stem Cells. 2001;19(4):279-86.

Sato et al., Maintenance of pluripotency in human and mouse embryonic stem cells through activation of Wnt signaling by a pharmacological GSK-3-specific inhibitor. Nat Med. Jan. 2004;10(1):55-63. Epub Dec. 21, 2003.

Schwartz et al., Defined conditions for development of functional hepatic cells from human embryonic stem cells. Stem Cells Dev. Dec. 2005;14(6):643-55.

Semenza et al., Regulation of cardiovascular development and physiology by hypoxia-inducible factor 1. Ann N Y Acad Sci. Jun. 30, 1999;874:262-8.

Shih et al., Human embryonic stem cells are prone to generate primitive, undifferentiated tumors in engrafted human fetal tissues in severe combined immunodeficient mice. Stem Cells Dev. Dec. 2007;16(6):893-902.

Shirahashi et al., Differentiation of human and mouse embryonic stem cells along a hepatocyte lineage. Cell Transplant. 2004;13(3):197-211.

Silván et al., Hypoxia and pluripotency in embryonic and embryonal carcinoma stem cell biology. Differentiation. Sep.-Oct. 2009;78(2-3):159-68. Epub Jul. 14, 2009.

Soto-Gutierrez et al., Differentiation of human embryonic stem cells to hepatocytes using deleted variant of HGF and poly-amino-urethane-coated nonwoven polytetrafluoroethylene fabric. Cell Transplant. 2006;15(4):335-41.

Spagnoli et al., Guiding embryonic stem cells towards differentiation: lessons from molecular embryology. Curr Opin Genet Dev. Oct. 2006;16(5):469-75. Epub Aug. 17, 2006.

Tian et al., Hematopoietic engraftment of human embryonic stem cell-derived cells is regulated by recipient innate immunity. Stem Cells. May 2006;24(5):1370-80. Epub Feb. 2, 2006.

West et al., In vitro gametogenesis from embryonic stem cells. Curr Opin Cell Biol. Dec. 2004;16(6):688-92.

Wion et al., pO$_2$ matters in stem cell culture. Cell Stem Cell. Sep. 4, 2009;5(3):242-3.

Wolff et al., Microelectrode measurements of pericellular pO$_2$ in erythropoietin-producing human hepatoma cell cultures. Am J Physiol. Nov. 1993;265(5 Pt 1):C1266-70.

Xu et al., Basic FGF and suppression of BMP signaling sustain undifferentiated proliferation of human ES cells. Nat Methods. Mar. 2005;2(3):185-90. Epub Feb. 17, 2005.

Xu et al., BMP4 initiates human embryonic stem cell differentiation to trophoblast. Nat Biotechnol. Dec. 2002;20(12):1261-4. Epub Nov. 11, 2002.

Yoon et al., Enhanced differentiation of human embryonic stem cells into cardiomyocytes by combining hanging drop culture and 5-azacytidine treatment. Differentiation. Apr. 2006;74(4):149-59. Erratum in: Differentiation. Jul. 2006;74(6):322.

Yoshida et al., Hypoxia enhances the generation of induced pluripotent stem cells. Cell Stem Cell. Sep. 2009 ;5(3):237-41. Epub Aug. 27, 2009.

Zandstra et al., Scalable production of embryonic stem cell-derived cardiomyocytes. Tissue Eng. Aug. 2003;9(4):767-78.

Zhou et al., A gene regulatory network in mouse embryonic stem cells. Proc Natl Acad Sci U S A. Oct. 16, 2007;104(42):16438-43. Epub Oct. 10, 2007.

* cited by examiner

SEQUENCE LISTING

<160> NUMBER OF SEQ ID NOS: 12

<210> SEQ ID NO 1
<211> LENGTH: 20
<212> TYPE: DNA
<213> ORGANISM: Mus musculus

<400> SEQUENCE: 1
tcccggtgct gaaggtaaat                                                    20

<210> SEQ ID NO 2
<211> LENGTH: 19
<212> TYPE: DNA
<213> ORGANISM: Mus musculus

<400> SEQUENCE: 2
ccgtcacgaa gtccagcaa                                                     19

<210> SEQ ID NO 3
<211> LENGTH: 22
<212> TYPE: DNA
<213> ORGANISM: Mus musculus

<400> SEQUENCE: 3
tcaaggccta cgaacaggtc at                                                 22

<210> SEQ ID NO 4
<211> LENGTH: 19
<212> TYPE: DNA
<213> ORGANISM: Mus musculus

<400> SEQUENCE: 4
gcccgctttg ttcgtgact                                                     19

<210> SEQ ID NO 5
<211> LENGTH: 25
<212> TYPE: DNA
<213> ORGANISM: Mus musculus

<400> SEQUENCE: 5
agatgctgaa gaaggtccag tagag                                              25

<210> SEQ ID NO 6
<211> LENGTH: 20
<212> TYPE: DNA
<213> ORGANISM: Mus musculus

<400> SEQUENCE: 6
caccaagttg ggcatgaaga                                                    20

<210> SEQ ID NO 7
<211> LENGTH: 20
<212> TYPE: DNA
<213> ORGANISM: Mus musculus

<400> SEQUENCE: 7
gcttccgctg tccagagact                                                    20

<210> SEQ ID NO 8
<211> LENGTH: 20
<212> TYPE: DNA
<213> ORGANISM: Mus musculus

<400> SEQUENCE: 8
tgccagcaga ttccatacca                                                    20

<210> SEQ ID NO 9
<211> LENGTH: 19
<212> TYPE: DNA
<213> ORGANISM: Homo sapiens

-continued

```
<400> SEQUENCE: 9
tgggctcgag aaggatgtg                                              19

<210> SEQ ID NO 10
<211> LENGTH: 20
<212> TYPE: DNA
<213> ORGANISM: Homo sapiens

<400> SEQUENCE: 10
gcatagtcgc tgcttgatcg                                             20

<210> SEQ ID NO 11
<211> LENGTH: 23
<212> TYPE: DNA
<213> ORGANISM: Homo sapiens

<400> SEQUENCE: 11
gcaaatgtct tctgctgaga tgc                                         23

<210> SEQ ID NO 12
<211> LENGTH: 20
<212> TYPE: DNA
<213> ORGANISM: Homo sapiens

<400> SEQUENCE: 12
ccatggagga gggaagagga                                             20
```

METHODS AND COMPOSITIONS FOR INCREASED SAFETY OF STEM CELL-DERIVED POPULATIONS

FIELD OF INVENTION

The invention provides methods and compositions relating to differentiated cell populations that derive from pluripotent stem cells. The methods relate to reducing the number of residual stem cells present in such populations. The compositions include differentiated cell populations that contain reduced number of stem cells or that contain no stem cells. Pluripotent stem cells may be reduced in number and/or function through exposure to low oxygen levels.

BACKGROUND OF INVENTION

Much research and clinical investigation is currently focused on the use of stem cells and their differentiated progeny. As an example, there are a variety of therapeutic approaches contemplated and/or being developed that involve the use of embryonic (ES) stem cells and/or their progeny. ES cells are pluripotent cells that have the ability to generate any cell type in a mature organism. The clinical potential for stem cell based therapies is immense (Lawrenz et al. Cytotherapy 6, 212-22 (2004)), including treatments for heart disease, diabetes, Parkinson's disease, and leukemia (Hentze et al. Trends Biotechnol 25, 24-32 (2007); Pei et al. J Biol Chem 284, 3365-9 (2009); Jaenisch et al. Cell 132, 567-82 (2008)). However, stem cells such as ES cells pose the risk of tumor formation upon implantation. For example, as few as two ES cells have been shown to form tumors in severe combined immunodeficiency (SCID) mice (Lawrenz et al. Cytotherapy 6, 212-22 (2004)).

SUMMARY OF INVENTION

The invention provides a novel and unexpected approach to reducing the frequency of pluripotent stem cells, such as but not limited to ES cells, in a population of cells intended for in vivo administration or for in vitro uses such as drug testing and/or screening. Typically, the cell population intended for in vivo administration is derived from the differentiation of one or more pluripotent stem cells. It therefore at least contains differentiated progeny of pluripotent stem cells and also contains (or is likely to contain) residual pluripotent stem cells. The frequency of residual pluripotent stem cells is reduced by long-term exposure to an oxygen partial pressure that is less than 142 mmHg (i.e., the oxygen partial pressure in a humidified incubator with an inlet gas containing 5% $CO_2$ and remainder air at 37° C., otherwise referred to herein as a normoxic condition). Usually this exposure will occur in vitro and will be referred to herein as culture at low oxygen partial pressure. The invention is therefore premised in part on the unexpected finding that exposure of a differentiated cell population to low oxygen partial pressure for extended periods of time does not compromise the quality or function of the differentiated cells in the population and rather serves to reduce residual pluripotent stem cells resident in the population, whether by further differentiation or by other means. This finding indicates that differentiated cell populations suspected of containing pluripotent stem cells can be treated in order to reduce and preferably eliminate such pluripotent stem cells without adverse effect on the differentiated cells within the population. The resultant cell population can then be used in vivo with a reduced risk, and preferably without risk, of tumor formation.

These findings also indicate that protocols for differentiating pluripotent stem cells may be modified to include at least a period of time in which the pluripotent stem cells and/or their progeny are exposed to low oxygen partial pressure. In this way, the pluripotent stem cells are differentiated as desired and in the process the numbers of such pluripotent stem cells are also reduced, thereby generating a differentiated cell population suitable for in vitro and/or in vivo use as described herein. In some embodiments, the pluripotent stem cells are differentiated towards non-cardiomyocyte lineages such as but not limited to neural cells, islet cells, and the like. In still other embodiments, the differentiation protocol is one carried out at normoxic conditions but for the findings of (and modifications provided by) the instant invention.

Thus, in one aspect, the invention provides a method comprising culturing a differentiated cell population at an oxygen partial pressure that is less than 142 mmHg for 20 days or more. In another aspect, the invention provides a method comprising culturing a differentiated cell population at an oxygen partial pressure that is less than 142 mmHg for 10 days or more, wherein the differentiated cell population is a non-cardiomyocyte differentiated cell population.

In another aspect, the invention provides a method comprising differentiating pluripotent stem cells towards a non-cardiomyocyte lineage in the presence of one or more differentiation stimuli at an oxygen partial pressure that is less than 142 mmHg. In another aspect, the invention provides an improved method for differentiating pluripotent stem cells comprising differentiating pluripotent stem cells in the presence of one or more differentiation stimuli and at an oxygen partial pressure that is less than 142 mmHg, wherein the improvement relates to exposing the cells to an oxygen partial pressure that is less than 142 mmHg in order to reduce pluripotent stem cell number following sufficient differentiation. In some embodiments, the pluripotent stem cells are exposed to the one or more differentiation stimuli and an oxygen partial pressure that is less than 142 mmHg simultaneously. In some embodiments, the pluripotent stem cells are exposed to the one or more differentiation stimuli and an oxygen partial pressure that is less than 142 mmHg separately.

In another aspect, the invention provides a method comprising culturing an isolated in vitro differentiated cell population at an oxygen partial pressure that is less than 142 mmHg for 10 days or more. An in vitro differentiated cell population is a cell population that is differentiated in vitro, as described herein.

Various embodiments apply to the foregoing aspects and these are recited below.

In some embodiments, the differentiated cell population is isolated from a differentiation culture.

In some embodiments, the differentiated cell population is derived from an embryonic stem cell or an induced pluripotent stem cell. In some embodiments, the differentiated cell population is derived from a human embryonic stem cell or a human induced pluripotent stem cell.

In some embodiments, the differentiated cell population comprises cardiomyocyte lineage cells. In some embodiments, the differentiated cell population comprises cardiomyocyte precursor cells. As used herein, the terms precursors and progenitors are used interchangeably. In some embodiments, the differentiated cell population comprises neural cells. In some embodiments, the differentiated cell population comprises islet cells. In some embodiments, the differentiated cell population comprises hepatic cells.

In some embodiments, the differentiated cell population comprises non-stem cell precursor cells. As used herein, non-stem precursors are cells that are not pluripotent stem cells yet are not terminally differentiated cells. Non-stem precursors include cells that are committed to one or more lineages and that have proliferative capacity.

In some embodiments, the oxygen partial pressure is 4-10 mmHg. In some embodiments, the oxygen partial pressure is 7 mmHg. In some embodiments, the oxygen partial pressure is 10-50 mmHg. In some embodiments, the oxygen partial pressure is 36 mmHg. In some embodiments, the oxygen partial pressure is 50-100 mmHg. In some embodiments, the oxygen partial pressure is 100-140 mmHg.

In some embodiments, the differentiated cell population is cultured for 20 days. In some embodiments, the differentiated cell population is cultured for 30 days. In some embodiments, the differentiated cell population is cultured for 40 days.

In some embodiments, the culturing step reduces pluripotent stem cells in the differentiated cell population by at least 2-fold, or at least 5-fold, or at least 10-fold, or at least 20-fold, or at least 40-fold, or at least 100-fold, or at least 150-fold.

In some embodiments, the method further comprises performing a positive selection for differentiated cells prior to, during and/or after the culturing step. In some embodiments, the method further comprises performing a negative selection for pluripotent stem cells prior to, during and/or after the culturing step. In some embodiments, the positive or negative selection is based on cell surface expression of a marker. In some embodiments, the positive or negative selection is a fluorescent activated cell sorting (FACS) selection. In some embodiments, negative selection is based on expression of SSEA-4, TRA-60 and/or Oct4. In some embodiments, the positive or negative selection is based on a physical property. In some embodiments, the negative selection is based on buoyant density.

In some embodiments, the method further comprises harvesting the differentiated cell population after the culturing step.

In some embodiments, the method further comprises assaying for teratoma-causing cells in the cultured differentiated cell population. In some embodiments, the teratoma-causing cells are assayed by introducing the cultured differentiated cell population into an immunocompromised mouse. In some embodiments, $10^3$ cells, $10^4$ cells, $10^5$ cells, $10^6$ cells, or $10^7$ cells from the cultured differentiated cell population are introduced into the immunocompromised mouse.

In some embodiments, the method further comprises measuring mRNA or protein expression of a stem cell marker in the cultured differentiated cell population. In some embodiments, the stem cell marker is Oct4.

In some embodiments, the method further comprises administering the differentiated cell population to a subject in need thereof.

In some embodiments, the differentiated cell population is cultured in a culture vessel comprising an oxygen permeable membrane. In some embodiments, the differentiated cell population is cultured in a culture vessel comprising a silicon rubber membrane.

In another aspect, the invention provides a differentiated cell population obtained according to any of the foregoing methods.

In another aspect, the invention provides an isolated differentiated cell population derived from isolated pluripotent stem cells and having less than 1 pluripotent stem cell per $10^3$ cells. In some embodiments, the differentiated cell population comprises less than 1 pluripotent stem cell per $10^4$ cells. In some embodiments, the differentiated cell population comprises less than 1 pluripotent stem cell per $10^5$ cells. In some embodiments, the differentiated cell population comprises less than 1 pluripotent stem cell per $10^6$ cells. In some embodiments, the differentiated cell population comprises less than 1 pluripotent stem cell per $10^7$ cells. In some embodiments, the differentiated cell population comprises less than 1 pluripotent stem cell per $10^8$ cells. In some embodiments, the differentiated cell population comprises less than 1 pluripotent stem cell per $10^9$ cells.

In some embodiments, the pluripotent stem cells are embryonic stem cells or induced pluripotent stem cells. In some embodiments, the pluripotent stem cells are human embryonic stem cells or human induced pluripotent stem cells.

In some embodiments, the differentiated cell population comprises cardiomyocyte lineage cells. In some embodiments, the differentiated cell population comprises cardiomyocyte precursor cells. In some embodiments, the differentiated cell population comprises neural cells. In some embodiments, the differentiated cell population comprises islet cells. In some embodiments, the differentiated cell population comprises non-stem cell precursor cells.

In another aspect, the invention provides a pharmaceutical preparation comprising any of the foregoing differentiated cell populations. In some embodiments, the preparation comprises at least $10^7$, at least $10^8$, or at least $10^9$ cells. In some embodiments, the preparation comprises a pharmaceutically acceptable carrier. In some embodiments, the differentiated cell population is isolated from its differentiation culture conditions. In some embodiments, the differentiated cell population is encapsulated in a gel. In some embodiments, the preparation is formulated for parenteral administration.

In another aspect, the invention provides a method for treating a subject comprising administering to a subject in need thereof a differentiated cell population produced according to any of the foregoing methods in an effective amount to treat the subject.

In another aspect, the invention provides a method comprising exposing any of the foregoing differentiated cell populations or any of the differentiated cell populations produced according to any of the foregoing methods to an agent, and determining the effect of the agent on the differentiated cell population. In some embodiments, determining the effect of the agent comprises determining the cytotoxicity of the agent on the differentiated cell population.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF DRAWINGS

It is to be understood that the Figures are not necessarily to scale, emphasis instead being placed upon generally illustrating the various concepts discussed herein.

FIG. 1A: Fraction of cells that are Oct4-GFP+ as measured with flow cytometry (n=3). FIGS. 1B and 1D: En face bright field images of cell aggregates after 20 days extended culture. FIGS. 1C and 1E: En face fluorescence images taken with a GFP filter corresponding with FIG. 1B and FIG. 1D, respectively. FIGS. 1F and 1G: Relative expression of Oct4 and Nanog mRNA measured with real-time PCR (n=3).

FIG. 3A: mESC differentiated at 142 mmHg $pO_{2gas}$ and then exposed to extended culture for 20 days at either 142 mmHg (black bar) or 7 mmHg (white bar). FIG. 3B: mESC differentiated at 7 mmHg $pO_{2gas}$ and then exposed to extended culture for 20 days at either 7 mmHg (black bar) or 142 mmHg (white bar). Data acquired with flow cytometry. * indicates significant difference compared to the black bar of the same time (n=3).

FIG. 4A: Formation of tumors after implantation of undifferentiated mESC (n=6; positive control), mESC differentiated 10 days at 142, 36, or 7 mmHg followed by 20 days extended culture at the same $pO_{2gas}$ (n=8) or only Matrigel (n=6; negative control). Tumor formation was determined by visual observation of the appearance of masses underneath the skin. FIG. 4B: Representative H&E-stained tissue section of a tumor derived from mESC differentiated and having undergone 20 days of extended culture at 7 mmHg $pO_{2gas}$, with (i) small glandular structure, (ii) hyaline cartilage, and (iii) neuroepithelial structures highlighted.

FIG. 5A: Fraction of mESC that are Oct4-GFP+ as measured with flow cytometry before sorting (unsorted) and after being sorted into an Oct4-GFP− population (sorted GFP−) (n=3). FIGS. 5B and 5C: $10^5$ cells were implanted without sorting (unsorted; n=8) or $10^5$ cells were sorted into GFP+ and GFP− populations (n=6), then implanted.

FIG. 6A: Fraction of cells that are Oct4-GFP+, as measured with flow cytometry (n=3). FIG. 6B: Formation of tumors after implantation of $10^5$ unsorted cells or cells sorted into SSEA-1+ and SSEA-1− populations (n=6).

FIG. 7A: Relative expression of Oct4 and Nanog mRNA measured with real-time PCR (n=3). FIG. 7B: Formation of tumors after implantation of undifferentiated HIF-1α$^{-/-}$ mESC (n=6; positive control) and HIF-1α$^{-/-}$ mESC differentiated 10 days at 142 or 7 mmHg followed by 20 days extended culture at the same $pO_{2gas}$ (n=6).

FIG. 8A: Histogram of the distribution of Oct4-GFP fluorescence intensity per cell, determined with flow cytometry. FIG. 8B: Fraction of cells that are Oct4-GFP+ after 0 and 10 days of differentiation at 142 mmHg $pO_{2gas}$ (n=3). FIGS. 8C to 8F: En face images of colonies from cell population II. FIG. 8C: Bright field image. FIGS. 8D to 8F: Cells stained with DAPI and immunostained for FIG. 8D: Oct4, FIG. 8E: Nanog, and FIG. 8F: SSEA-1.

FIG. 9B: Foxa2, and FIG. 9C: Nestin after 4 days of differentiation and FIG. 9D: cTnT, FIG. 9E: cardiac-α-Actin, and FIG. 9F: Nkx2.5 after 10 days of differentiation. (n=3).

FIGS. 10A to 10D: 4 days and FIGS. 10E and 10F: 10 days of differentiation stained with DAPI (FIGS. 10A, 10C, and 10E) and immunostained for FIG. 10B: Foxa2, FIG. 10D: Nestin, and FIG. 10F: cTnT.

FIG. 11A: Fraction and FIG. 11B: number of Nestin+ cells after 4 days of differentiation. FIG. 11C: Fraction and FIG. 11D: number of MF-20+ cells after 10 days of differentiation. (n=3).

FIGS. 12A and 12B: Relative expression of OCT4 and NANOG mRNA measured with real-time PCR (n=3). FIG. 12C: Formation of tumors after subcutaneous implantation of undifferentiated hESC (positive control; n=6) and hESC differentiated 30 days at 142, 36, or 7 mmHg (n=6). This data was obtained through 55 days after implantation.

DETAILED DESCRIPTION OF INVENTION

Figure 1A:
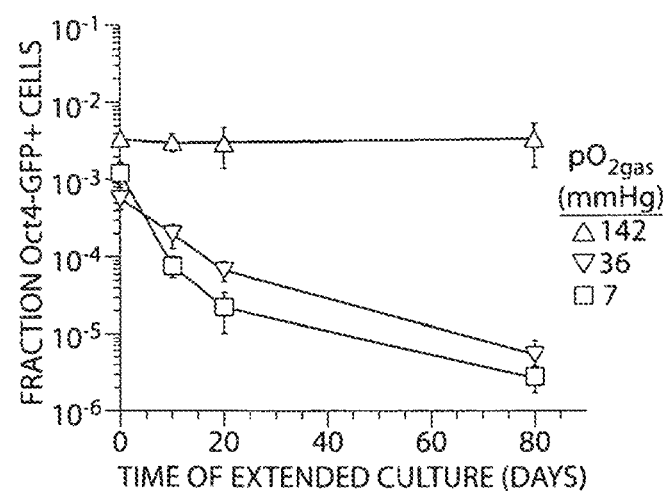
FIGS. 1A to 1G. Expression of pluripotency markers in mESC having undergone differentiation and extended culture at various $pO_{2gas}$. mESC were differentiated at 142, 36, or 7 mmHg $pO_{2gas}$ then subjected to 0, 10, 20, or 80 days of extended culture at the same $pO_{2gas}$.

The invention provides, in part, methods for increasing the safety of cell populations intended for in vivo use. More specifically, the safety of such populations is increased by reducing the number (and typically frequency) of tumor-causing cells in the population. These tumor-causing cells are pluripotent stem cells or their close or more immediate generational progeny. The population intended for use in vivo or in vitro, as provided herein, are more differentiated and committed progeny of such stem cells. It is well known that pluripotent stem cells, such as ES cells, are able to form tumors in vivo. These tumors may be teratomas or teratocarcinomas (Damjanov et al. Nat. Biotechnol. 25(11):1212 (2007); Lensch et al. Nat Biotechnol 25(11); 1211 (2007)). These tumors typically comprised of all three germ layers (i.e., mesoderm, ectoderm and endoderm). For convenience and brevity, tumors generated by pluripotent stem cells are referred to primarily as teratomas however it is to be understood that such teachings equally apply to teratocarcinomas. As a result, the in vivo use of cell populations derived from the differentiation of stem cells is limited by the presence of residual stem cells. The invention provides methods for overcoming this limitation, as described below.

The invention therefore provides in part methods that involve exposure of a differentiated cell population to low oxygen partial pressure for extended periods of time. It has been found in accordance with the invention that subjecting a differentiated cell populations to low oxygen partial pressure for extended periods of time does not lead to cell death of the differentiated cells, and this approach is therefore a suitable manipulation of populations intended for in vivo use.

The invention further contemplates modification of protocols for differentiating pluripotent stem cells into one or more lineages by combining such protocols with low oxygen partial pressure exposure. Such protocols typically occur at normoxic conditions, as defined herein, and thus are not dependent on low oxygen partial pressure to differentiate pluripotent stem cells. Examples of such differentiation protocols are provided herein. In most instances, such differentiation protocols involve exposure of pluripotent stem cells to one or more differentiation stimuli. As used herein, a differentiation stimulus is a stimulus other than low oxygen partial pressure. Such differentiation stimuli may be chemical agents (e.g., retinoic acid, valproic acid, etc.), biological agents (e.g., growth factors, cytokines, interleukins, etc.), and the like. According to the invention, exposure to such stimuli may occur at the same time or at a different time as the exposure to low oxygen partial pressure. Thus, in one example, the differentiation protocol includes exposing pluripotent stem cells to one or more differentiation stimuli under a normoxic condition and then under a low oxygen partial pressure condition. In another example, the differentiation protocol includes exposing pluripotent stem cells to a low oxygen partial pressure condition and then to a normoxic condition, all the while exposing the cells to one or more differentiation stimuli. The oxygen partial pressure may be cycled between normoxic and low oxygen partial pressure throughout the differentiation protocol in either example. In other examples, the differentiation protocol is performed under low oxygen partial pressure throughout. In some of these latter examples, the differentiation protocol does not differentiate pluripotent stem cells into the cardiomyocyte lineage. In other examples, the differentiation protocol may expose pluripotent stem cells (and their progeny) to a differentiation stimulus under normoxic conditions, followed by exposure to low oxygen partial pressure whether in the presence or absence of the differentiation stimulus. The invention contemplates a variety of such methods. Exposure to low oxygen partial pressure according to these various embodiments may occur for 1, 2, 3, 4, 5, 6, 7, 8, 9, or 10 or more contiguous or non-contiguous days, or it may occur for at least 1%, 2%, 3%, 4%, 5%, 10%, 15%, 20%, 25%, 30%, 40%, 50%, 75%, 80%, 90%, 95% or 100% of the culture time or the exposure time to the one or more differentiation stimuli.

Thus, in some aspects, the invention provides an improvement to the protocols used to differentiate pluripotent stem cells at normoxic conditions. The improvement comprises performing a part or all of the differentiation protocol at an oxygen partial pressure that is less than 142 mmHg. This improvement results in fewer residual pluripotent stem cells in the resultant differentiated cell population. The ability to overlay (or concurrently apply) differentiation stimuli and low oxygen partial pressure can preclude the need to perform two consecutive steps thereby saving time.

Although not intending to be bound by any particular theory or mechanism, one possible explanation for the effect of low oxygen partial pressure on residual stem cells is that low oxygen partial pressure causes loss of pluripotency by driving differentiation of any residual stem cells. Another possibility is that low oxygen partial pressure is selectively killing the residual stem cells while sparing the majority of differentiated cells in the population.

As will be understood in the art, upon cell division, pluripotent stem cells have the capacity to self-renew and/or differentiate. In its broadest sense, "differentiation" in this context implies that the daughter cell has lost its ability to self-renew and typically has started to commit to one or more lineages (i.e., it has lost its pluripotent capacity). "Self-renewal" on the other hand implies that the daughter cell (like its stem cell parent) maintains the ability to self-renew and is pluripotent. Stem cell division may be symmetric or asymmetric. If symmetric, then the result is two daughter cells that are both stem cells or two daughter cells that are both committed. If asymmetric, then the result is one daughter cell that is a stem cell (i.e., it is pluripotent and can self-renew) and one daughter cell that committed. Differentiation (but not self-renewal) may also occur in the absence of cell division. Thus, the invention contemplates that any residual stem cells residing in a differentiated cell population may differentiate upon exposure to long-term reduced oxygen partial pressure whether in the presence or absence of proliferation.

Surprisingly, the low oxygen partial pressure exposure apparently has no deleterious effect on the viability of the majority of the differentiated cell population and no apparent deleterious effect on function. As shown in the Examples, a cardiomyocyte differentiated population derived from pluripotent stem cells demonstrate contractile function before and after exposure to low oxygen partial pressure. This is true regardless of the nature of the protocol used to generate the differentiated cells in the first instance. Thus while the Examples illustrate reduction in residual stem cell numbers in a population of cells that comprise cardiomyocytes and cardiomyocyte precursors derived from pluripotent stem cells in vitro using low oxygen conditions, the invention is not limited to these differentiated cell types or to cells differentiated using low oxygen.

The invention therefore provides methods for reducing the number and frequency of pluripotent stem cells in cell populations by exposing such populations to low oxygen partial pressure. As will be understood, the selective reduction in stem cell numbers observed in differentiated cell populations in accordance with the invention correlate with reduction in stem cell frequency since the remaining cells in the population are apparently spared. As a result, the invention may refer to reduced stem cell number or stem cell frequency, in various aspects or embodiments. These methods provided herein can be used to reduce the risk of tumor formation upon in vivo administration of the cell population. These methods will in turn allow for higher numbers of cells to be administered to subjects with reduced risk (or in some instances without risk) of tumor formation.

The invention also provides cell populations derived from pluripotent stem cells and having no pluripotent stem cells or reduced pluripotent stem cells (e.g., compared to a differentiated cell population that is not exposed to a low oxygen partial pressure). The differentiated cells within this population will typically not be compromised, whether in number or function, by the exposure to low oxygen partial pressure. In other words, the differentiated cells will still be usable for one or more intended in vitro (e.g., drug screening or testing) or in vivo (e.g., tissue regeneration) purposes.

The invention further provides methods for using such "treated" cell populations in vivo (e.g., for preventative or therapeutic purposes), as well as uses of such cell populations in the making of medicaments for the prevention and/or treatment of certain disorders. The invention further contemplates methods for using the treated cell populations in vitro (e.g., in screening methods).

In still other aspects, the invention provides methods for monitoring reduction in stem cell number and/or function by subjecting a cell population to low oxygen partial pressure for an extended period of time by for example testing the tumorigenic content of the population by administering (typically by injection) all or part (i.e., an aliquot) of the population to a mouse such as but not limited to an immunocompromised mouse, and determining whether and when a tumor forms at the site of administration.

The invention provides alternative or additional methods for monitoring reduction in stem cell number and/or function after extended exposure to low oxygen partial pressure by monitoring the expression of early stem cell markers such as Oct4 (also known as POU5F1), Sox2, Nanog, SSEA-1 (for mouse), SSEA-4 (for human), Stat3, Hesx1, Zic3, Tra-1-60, Tra-1-80 and alkaline phosphatase. In some particular embodiments, Oct4, Nanog or Sox2, or some combination thereof are monitored (Jaenisch et al. Cell 132(4): 567-82 (2008)). The target genes of Oct4, Sox2 and Nanog can also be monitored. Such target genes are described in Boheler J Cell Physiol 10.1002/jcp.21866 (2009) and are incorporated by reference herein. Such markers are indicative of the presence of pluripotent stem cells and thus may be used as surrogate markers for pluripotent stem cell content and/or tumorigenic activity in the population.

The invention further provides cell populations derived from the differentiation of pluripotent stem cells that have no or reduced numbers of residual pluripotent stem cells.

The invention contemplates performing the low oxygen partial pressure "tumor cell reduction step" on any differentiated cell population derived from and having (or suspected of having) residual pluripotent stem cells. In some instances, the nature of the differentiation protocol used to generate the differentiated cell population is known. In other instances, it may not be known. The invention is not dependent on the nature of such protocol.

Based on the findings and teachings provided herein, those of ordinary skill in the art will understand that the extent of tumor-cell reduction (e.g., as controlled by the level of oxygen partial pressure and the time of exposure to low oxygen partial pressure) will depend on the nature of the differentiated cell population, the degree of tumor-cell reduction desired, and the ultimate use of the resultant population. The desired frequency may be 1 in $10^4$, 1 in $10^5$, 1 in $10^6$, 1 in $10^7$, 1 in $10^8$, 1 in $10^9$, or even lower. These frequencies will dictate in part the length of time of the low oxygen exposure.

Thus, the invention contemplates first generating a cell population from one or more pluripotent stem cells through the differentiation of such stem cells, and then exposing the generated cell population to low oxygen partial pressure for extended periods of time in order to reduce the number and/or pluripotent capacity of residual stem cells.

In some instances, the differentiated cell population is isolated from its differentiation culture conditions and then placed into low oxygen partial pressure conditions. In some instances, the differentiated cell population is not isolated from its differentiation culture conditions and rather the conditions are changed to low oxygen partial pressure conditions as taught herein. In some instances, differentiated cell populations treated in this latter manner may exclude those that are differentiated using only low oxygen partial pressure. If the differentiated cell population was generated using a protocol that involved low oxygen partial pressure exposure, then this population may be treated according to the invention in order to reduce residual pluripotent stem cells by exposure to low oxygen partial pressure for longer periods of time including for example 20, 25, 30, 35, 40, 45, 50 or more days. In some embodiments, populations differentiated using only low oxygen partial pressure may comprise cardiomyocyte and/or cardiomyocyte precursors. If the differentiated cell population was generated using a protocol that involved exposure to normoxic conditions as a last step, then this population may be treated according to the invention in order to reduce residual pluripotent stem cells.

Pluripotent Stem Cells

According to the invention, cell populations are exposed to low oxygen partial pressure in order to reduce the risk of tumor formation from pluripotent stem cells upon in vivo administration. Pluripotent stem cells may be referred to herein as stem cells for brevity. Pluripotent stem cells, as discussed above, are cells that are both capable of self-renewal (i.e., generating, upon cell division, one or two cells with self-renewal and pluripotent capacity) and pluripotent (i.e., they have the ability to differentiate into mesoderm, ectoderm and endoderm lineages). It is to be understood that the invention contemplates and can be carried out using cell populations derived from pluripotent stem cells which in turn are derived from embryonic tissue (such as ES cells), pluripotent stem cells derived from the dedifferentiation of adult cells (such as induced pluripotent stem (iPS) cells), as well as other forms of pluripotent stem cells. ES cells are pluripotent stem cells derived from the inner cell mass of blastocysts and propagated in vitro. These cells have the capacity to differentiate into any cell type in the body. The invention contemplates other pluripotent stem cells including those resulting from somatic cell nuclear transfer (e.g., transfer of a nucleus from a somatic cell of a subject into an enucleated embryo), parthenogenesis, androgenesis or other asexual techniques. The invention contemplates the use of ES cells from these various sources although aspects, embodiments and exemplifications of the invention are discussed in the context of pluripotent stem cells that are ES cells, for the sake of brevity.

The invention contemplates the use of pluripotent stem cells from any species that may be treated using differentiated progeny of such stem cells. Such species include human, and various animal species including household species such as dogs and cats, agricultural species such as cows, pigs, and horses, laboratory species such as mice and rats, and the like.

The pluripotent stem cells may be genetically manipulated (e.g., they may be transfected) or they may not be genetically manipulated. Transfection refers to genetic manipulation of cells to introduce and typically express an exogenous nucleic acid. The exogenous nucleic acid may be a reporter such as green fluorescent protein (GFP) or it may be a selection marker such as thymidine kinase. It will be understood that in some instances reporters such as GFP may also serve as selection markers, particularly if their expression is controlled by pluripotent gene promoters such as an Oct4 promoter. The ES cells may be murine or human ES cells.

A number of ES cell lines currently exist. These include murine ES cell lines such as J1, R1, D3, CCE, SCC10, B6/Blu, EDJ22, and B6/GFP, and human ES cell lines such as BG01, BG02, BG03, SA01, SA02, ES01, ES02, ES03, ES04, ES05, ES06, H1, H9, TE03, TE04, TE06, UC01, UC06, WA01, WA07, WA09, WA13 and WA14. Reference may be made to the NIH Human ES Cell Registry which lists various human ES cell lines and whether and from whom such lines are available.

In addition, protocols for generating ES cells and lines are known in the art. The generation of murine ES cells and lines has been described. See for example Teratocarcinomas and ES cells: a practical approach (1987). E. J. Robertson, editor. IRL Press. and Wernig et al. Nature. 2007 Jun. 6 (online publication). U.S. Pat. Nos. 5,843,780 and 6,200,806 assigned to WARF describe the generation of human ES cells.

iPS cells are stem cells generated by reprogramming somatic cells such as fibroblasts to an earlier developmental stage. This reprogramming may occur through the induced ectopic expression of gene combinations such as OCT4, SOX2, KLF4 and MYC, or OCT4, SOX2, NANOG and MYC, or OCT4, SOX2, NANOG and LIN28. Reprogramming may involve chemical stimuli such as valproic acid. (Huangfu et al., 2008, Nat. Biotechnol., 26(11):1269-1275.) Phenotypically, iPS cells are small round translucent cells that preferably grow in vitro in colonies that are themselves characterized as tightly packed and sharp-edged. Genetically, iPS cells express markers of pluripotency such as OCT4 and NANOG, cell surface markers such as SSEA3, SSEA4, Tra-1-60, and Tra-1-80, and the intracellular enzyme alkaline phosphatase. These cells have a normal karyotype. Their cell cycle profile can be characterized by a short G1 phase, similar to that of hES cells. A number of iPS cell lines currently exist. These include iPS (Foreskin) (Clone 1), iPS(IMR90) (Clone 1), iPS(IMR90) (Clone 4), and the virus-vector free iPS—DF19-9 (Clone 7T), which can be purchased from WiCell Research Institute (Madison, Wis.). In addition, protocols for generating iPS cells and cell lines have been described. See for example Takahashi and Yamanaka, 2006, Cell 126(4):663-676; Wernig et al., 2007, Nature 448:7151; Okita et al., 2007 Nature 448:7151; Maherali et al., 2007 Cell Stem Cell 1:55-70; Lowry et al., 2008 PNAS 105:2883-2888; Park et al., 2008 Nature 451: 141-146.; Takahashi et al., 2007 Cell 131, 861-872; Yu et al., 2007 Science 318:5858.

The invention refers to isolated pluripotent stem cells. As used herein, isolated pluripotent stem cells are cells which have been physically separated from their environment. If the cells are naturally occurring, then isolation implies that the cells are physically separated from the naturally occurring environment from which they derive. In some instances, isolated stem cells are additionally or alternatively physically separated, in whole or in part, from an in vitro environment such as for example non-stem cells.

Thus, as used herein, the term isolated means that a molecule, cell, cell population and the like is physically separated from an environment in which it normally exists, or in which it originally or previously existed. Isolation may refer to physical separation of cells from a culture condition (e.g., a differentiation culture), from a naturally occurring environment or source, and the like. A differentiated cell population may be isolated from a differentiation culture condition, for example, by harvesting the cells and removing the culture medium (e.g., by centrifugation). Isolating may also involve washing the cells. Typically, the cells are resuspended in fresh medium. Isolation of the differentiated cell population from the differentiation culture therefore can serve to remove factors or stimuli used to differentiated the pluripotent stem cells towards one or more lineages.

The invention refers to tumor-forming cells which may be teratoma-forming cells or teratocarcinoma-forming cells. It is to be understood that these terms refer to cells that form (or have the capacity to form) tumors and in particular teratomas in vivo. Pluripotent stem cells are tumor-forming or teratoma-forming cells.

Differentiated Cell Population

The methods provided herein involve exposing a differentiated cell population to low oxygen partial pressure. As used herein, a differentiated cell population is a population of cells that is derived in vitro from pluripotent stem cells according to one or more differentiation protocols and that contains differentiated cells. Differentiated cells, as used herein, are cells that are not pluripotent stem cells, as described herein. Typically, a population of differentiated cells will have a phenotype or function associated with one or more cell lineages. For example, an example of a differentiated cell population is a population that comprises cells that are positive for a lineage specific marker. The marker may be associated with commitment to endoderm, mesoderm or ectoderm lineages, or it may be associated with trophoectoderm lineages, or it may be associated with commitment to specific lineages such as cardiomyocytes, islet cells, neuronal cells, and the like. An example of a cardiomyocyte specific marker is MF-20. Other markers for cardiomyocytes and other lineages are known in the art. The differentiated cells may comprise cells committed to one or more lineages, including terminally differentiated cells and/or uni-, bi- and/or multilineage precursors.

Differentiated cells may comprise 1%, 2%, 3%, 4%, 5%, 6%, 7%, 8%, 9%, 10%, 15%, 20%, 25%, 30%, 35%, 40%, 45%, 50%, or more of the cells in the differentiated cell population. The proportion of differentiated cells in the population may vary depending on the differentiation protocol. For example, the differentiated cells may represent 10%, 20%, 30%, 40%, 50%, 60%, 70%, 80%, 90%, or more of the cells in the population. The remaining cells may be differentiated cells of unknown lineage, unidentified cells, and/or residual pluripotent stem cells. Pluripotent stem cells therefore must represent less than 100% of the cells in the differentiated cell population. (In other words, a cell population that is 100% pluripotent stem cells is not a differentiated cell population.) More typically, pluripotent stem cells represent 0.5%, 1%, 2%, 3%, 4%, 5%, 6%, 7%, 8%, 9%, 10% or more (but less than 100%) of the cells in the differentiated cell population. In these latter instances, the invention seeks to reduce the frequency of pluripotent stem cells in the differentiated cell population to about 1 in $10^3$ total cells (or 0.1%), or 1 in $10^4$ total cells (or 0.01%), or 1 in $10^5$ total cells (or 0.001%), or 1 in $10^6$ total cells (or 0.0001%), or 1 in $10^7$ total cells (or 0.00001%), or 1 in $10^8$ total cells (or 0.000001%), or 1 in $10^9$ total cells (or 0.0000001%), or less.

In some embodiments, pluripotent stem cells represent 1%, 5%, 10%, 15%, 20%, 25%, 30%, 35%, 40%, 45%, 50%, or more (but less than 100%) of the differentiated cell population and the methods of the invention reduce the number (and accordingly frequency) of such pluripotent stem cells by 2-fold, 3-fold, 4-fold, 5-fold, 6-fold, 7-fold, 8-fold, 9-fold, 10-fold, 20-fold, 30-fold, 40-fold, 50-fold, 75-fold, 100-fold, 125-fold, 150-fold, or more.

It is to be understood that the methods of the invention may be applied to any differentiated cell population derived from pluripotent stem cells regardless of whether or not the presence of residual pluripotent stem cells has been confirmed in that population. That is, the invention does not require that the differentiated cell population be first tested for the presence of pluripotent stem cells prior to low oxygen exposure. Accordingly, the low oxygen methods provided herein may be applied to differentiated cell populations derived from pluripotent stem cells that are known to contain residual pluripotent stem cells or that may contain (including are likely to contain) pluripotent stem cells. As described in greater detail below, a person of ordinary skill in the art may assay the differentiated cell population prior to, during and/or following low oxygen exposure in order to determine the extent of pluripotent stem cell reduction.

Low Oxygen Partial Pressure

The invention contemplates exposing cell populations comprising (or suspected of comprising or likely to comprise) pluripotent stem cells to low oxygen partial pressure. As used herein, low oxygen partial pressure refers to an oxygen partial pressure that is less than 142 mmHg if exposure such as culture occurs in the presence of $CO_2$ and a bicarbonate-based buffer, or less than 160 mmHg if exposure such as culture occurs in the absence of $CO_2$ and with another buffer such as HEPES. As used herein, low oxygen partial pressure (or low $pO_2$) refers to a $pO_2$ that is less than 142 mmHg for cultures in the presence of 5% $CO_2$ (inlet gas). This level of $CO_2$ represents typical culture conditions in the art. In some embodiments, low $pO_2$ may be a $pO_2$ that is less than 140 mmHg, less than 120 mmHg, less than 100 mmHg, less than 80 mmHg, less than 70 mmHg, less than 60 mmHg, less than 50 mmHg, less than 40 mmHg, less than 30 mmHg, less than 20 mmHg, less than 10 mmHg or lower. In some embodiments, low $pO_2$ may be zero mmHg. $pO_2$ in the methods of the invention may be in the range of 0-80 mmHg, 0-70 mmHg, 0-60 mmHg, 5-80 mmHg, 5-70 mmHg, or 5-60 mmHg. $pO_2$ in the methods of the invention may be in the range of 5-50 mmHg, 10-50 mmHg, 20-50 mmHg, and 20-40 mmHg, including every integer therebetween (i.e., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 mmHg). In some embodiments, the $pO_2$ is about 7 mmHg or about 36 mmHg. As used in the context of $pO_2$ measurements, the term "about" indicates a difference with the indicated value in the range of 0-15 mmHg.

Typically, the oxygen partial pressure referred to herein refers to the oxygen partial pressure sensed by cells in culture. The most common way of modulating oxygen levels in a culture is by modulating the oxygen partial pressure in the gas phase of a culture system. Such oxygen partial pressure is referred to herein as $pO_{2gas}$. $pO_{2gas}$ can be regulated during culture using manual and automated devices. Examples of commercially available automated devices include but are not limited to OxyCycler C42 from BioSpherix (Redfield, N.Y.), OWJ2720A from Queue Systems (Parkersburg, Va.).

The oxygen partial pressure at the surface of a cell is referred to herein as $pO_{2cell}$. $pO_{2cell}$ depends on several factors including medium depth, cell density, cellular oxygen consumption rate, diffusion characteristics of the medium, and $pO_{2gas}$. Thus, in some instances, $pO_{2gas}$ is not indicative of or equivalent to the oxygen partial pressure experienced by cells in the liquid phase of the culture.

Cells grown in monolayers are more likely to be exposed to an oxygen partial pressure that approximates the gas phase oxygen partial pressure than are cells grown in a non-monolayer manner (e.g., in layers, spheres or aggregates). The difference between $pO_{2cell}$ and $pO_{2gas}$ for cells in a monolayer is typically due to diffusion gradients in the culture medium. Cells grown in a non-monolayer manner, particularly those buried within a sphere or aggregate, will have a $pO_{2cell}$ that is less than the $pO_{2gas}$ because of the internal oxygen gradients within the multiple layers of cells and/or aggregates.

Cells may be cultured under conditions in which $pO_{2cell}$ approximates $pO_{2gas}$ One way of accomplishing this is to enhance oxygen transport to cells in culture. For example, cells may be cultured under conditions where $pO_{2cell}$ of a cell layer or at the surface of a 3-dimensional aggregate is approximately equal to $pO_{2gas}$. This can be accomplished in number of ways, as will be discussed in greater detail below.

Various modifications to the culture system may be performed in order to reduce the difference between $pO_{2gas}$ and $pO_{2cell}$. Implementation of these methods therefore allow for reliance on $pO_{2gas}$ as the readout for $pO_{2cell}$. For example, convective oxygen transport in mechanically mixed or perfused vessels may be used, including stirring of and/or bubbling of oxygen through a culture medium. The cultures may be subject to in situ generation of oxygen using electrochemical hydrolysis of water or other means. Alternatively or additionally, culture vessels having one or more sides, walls and/or bottom to which cells attach and grow that comprise an oxygen permeable membrane can also be used. It is to be understood that the invention contemplates various culture vessel configurations involving oxygen permeability. These include without limitation bags comprising oxygen permeable membranes. As used herein, an oxygen-permeable membrane is a membrane that has an oxygen permeability greater than that of a standard (e.g., polystyrene) culture dish. One example of an oxygen-permeable membrane is a fluoroethylene-propylene copolymer (FEP-Teflon) membrane. Culture vessels comprising this membrane are commercially available as Lumox dishes (Greiner Bio-One, Munich). Another example of an oxygen-permeable membrane is a silicone rubber membrane, which is used in the Examples. The oxygen permeabilities of FEP Teflon and silicone rubber are $0.2$-$0.4 \times 10^{-14}$ and $26 \times 10^{-14}$ mol $cm^{-1}$ $mmHg^{-1}$ $sec^{-1}$, respectively.

It is to be understood that although small oxygen gradients may exist across the diameter of a cell, generally such gradients will be small enough that the oxygen partial pressure at the cell surface and within the cell can be considered to be essentially the same.

Figure 15A:
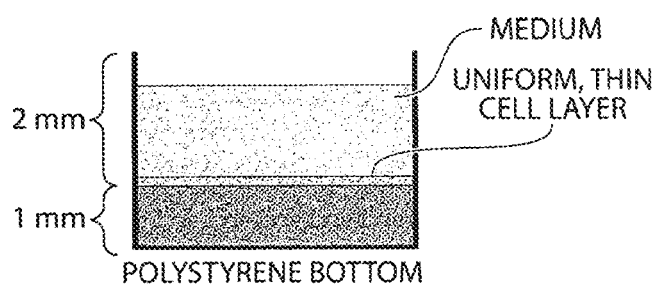
FIGS. 15A and 15B. Schematic representation of a polystyrene (FIG. 15A) and silicone rubber membrane-based (FIG. 15B) culture dish.
Figure 15B:
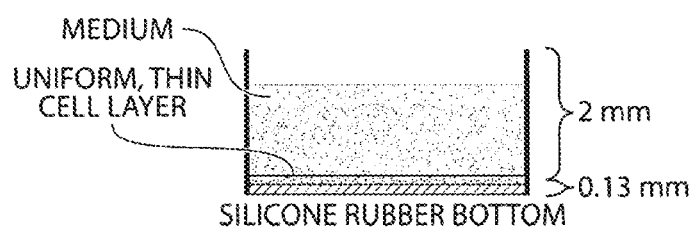

Silicone rubber culture vessels, as used herein, are culture vessels that comprise a silicone rubber membrane bottom. In other words, the internal face of the vessel to which the ES cells attach is made of silicone rubber. The advantage of silicone rubber is its high permeability to gases such as oxygen. An example of a silicone rubber culture vessel is a silicone rubber dish, described in the Examples. FIGS. 15A and 15B provides an exemplary schematic of a culture dish having a silicone rubber membrane bottom. In still other embodiments, an insert of such oxygen permeable membranes is placed in a culture vessel. Inserts of silicone rubber membranes are available from for example Wilson Wolf. Oxygen control may also be accomplished by the use of a perfluorocarbon layer for growing cells, or by any other method known in the art.

A silicone rubber bottom culture vessel such as that illustrated in FIGS. 15A and 15B may be made according to the following protocol. Silicone rubber sheeting can be purchased from Specialty Manufacturing (Saginaw, Mich.). The sheet is optically clear (gloss finish) and is 0.005 inches (127 μm) thick. Prior to use the membrane material is cut to the desired shape with scissors and sterilized by autoclaving for 30 minutes at 121° C. The bottom surface of the 8 central wells of 24-well tissue culture plates (353047, Becton Dickinson) is removed using a ⅜×3 inch fixed handle nutdriver (12, Cooper Hand Tools, Apex, N.C.) heated in a Bunsen burner. A sterile scalpel is used to trim the edges of the holes so that they are flush with the rest of the plate bottom. A very thin layer of silicone adhesive (59530, Henkel Loctite Corp., Rocky Hill, Conn.) is spread on the base of the plate around each of the holes. A rectangular 8.5×4.5 cm piece of silicone rubber sheeting (non-reinforced vulcanized gloss/gloss 0.005 inch, Specialty Manufacturing, Saginaw, Mich.), previously sterilized by autoclaving, is placed over the holes, and manually pressed/stretched so that the silicone sheet is flat (no wrinkles) and sealed onto the plate bottom. After allowing the adhesive to set for 24 hr, the plates are completely filled with a 70% ethanol solution for 1 hr and dried overnight under a germicidal UV lamp in a biological safety cabinet.

Oxygen partial pressure is generally referred to herein in units of mmHg. However many oxygen control devices associated with culture incubators express oxygen levels as a percentage. Generally $pO_{2gas}$ in mmHg can be determined based on knowledge of a percent oxygen measurement in the culture incubator using the following formula:

$$pO_2=[(\% \text{ oxygen})/(100\%)]\times(760 \text{ mmHg})$$

In this equation, 760 mmHg is the atmospheric pressure.

For a humidified environment at 37° C. (which is generally the case with culture incubators), $pO_{2gas}$ can be determined based on the composition of the oxygen at the incubator inlet measured as percent oxygen (usually specified by the content of a premixed compressed gas tank) using the following formula:

$$pO_2=[(\% \text{ oxygen})/(100\%)]\times(760-47.1 \text{ mmHg})$$

In this equation, 760 mmHg is the atmospheric pressure and 47.1 mmHg is the vapor pressure of water at 37° C. Inlet oxygen levels of 1%, 5%, 20%, and 40% correspond to $pO_{2gas}$ of 7.13 mmHg, 35.6 mmHg, 142 mmHg, and 285 mmHg in the humidified incubator. Inlet gas for a standard culture incubator is 19.9% oxygen (95% air and 5% $CO_2$), and $pO_{2gas}$ is therefore 142 mmHg.

In many cases, during cell culture in bioreactors, the % oxygen is actually given as % of air saturation. The equation to convert between the two is $$\% \text{ absolute}=\% \text{ air saturation}\times 0.209$$

In this equation, 0.209 is the volume fraction or mole fraction of oxygen under atmospheric conditions.

Culture Conditions and Times

Differentiated cell populations comprising (or suspected of comprising or likely to comprise) pluripotent stem cells are exposed to low oxygen partial pressure. This typically occurs while such populations are being cultured in vitro. Such cultures are usually performed at about 37° C., in incubators, as described herein. As described herein, the differentiated cell population is derived from the differentiation of pluripotent stem cells. Thus, it is to be understood that the low oxygen culture of the present invention is applied to a population of cells that already comprises a proportion of differentiated cells rather than a starting population of pluripotent stem cells. The methods of the invention may involve transferring cells to a new culture vessel although this is not essential (e.g., in some instances the differentiation step and the "pluripotent stem cell reduction" step may be carried out in the same vessel, and in other instances the two steps may be carried out in different vessels). Separate vessels and optionally wash of cells may be involved if the culture conditions are different between the two steps.

The exposure time (e.g., the culture period) may be 1 day, 2 days, 3 days, 4 days, 5 days, 6 days, 7 days, 8 days, 9 days, 10 days, 15 days, 20 days, 25 days, 30 days, 35 days, 40 days or more.

In other instances, the invention contemplates isolating a cell population that has been previously cultured in low oxygen partial pressure in order to form a differentiated cell population from its low oxygen partial pressure "differentiation" culture environment and then exposing it to low oxygen partial pressure for the purpose of reducing residual stem cell number. In still other instances, the invention contemplates culturing pluripotent stem cells (and their progeny) under low oxygen partial pressure followed by a period of normoxic oxygen partial pressure in order to differentiate the stem cells towards one or more lineages, and then culturing the resultant population under low oxygen partial pressure again in order to reduce the number of residual pluripotent stem cells in the population. In this latter instance, the cells may be isolated from the differentiation culture or they may be continuously maintained in the same culture environment with only the oxygen partial pressure changing. In these instances, the period of low oxygen partial pressure required to reduce pluripotent stem cell numbers may be 1, 2, 3, 4, 5, 6, 7, 8, 9, 10, 15, 20, 25, 30, 35, 40, or more days. As discussed herein, the length of culture will depend in part on the desired stem cell frequency ultimately desired by the end user of the differentiated cell population. As an example, some end users contemplating in vitro culture and/or testing of lower numbers of the differentiated population (e.g., $10^3$ or $10^4$ cells) may not need to culture as long as some end users contemplating in vivo administration of higher numbers of the population (e.g., $10^8$ or $10^9$ cells). As another example, some in vitro applications may require longer culture periods at low oxygen partial pressure than some in vivo applications. The invention contemplates these various possibilities.

In still other instances, pluripotent stem cells are differentiated under low oxygen partial pressure and then cultured under low oxygen partial pressure in order to reduce pluripotent stem cell number and/or function. In these instances, the cultures may be continuous and may be a total of 20, 25, 30, 35, 40, 45, 50, 55, 60 or more days. By continuous, it is meant that the cells are not isolated from the differentiation culture conditions and then recultured.

The culture may occur in culture vessels having oxygen-permeable bottom membranes (e.g., oxygen-permeable silicone rubber membrane). These vessels may be constructed so as to replace their bottoms with these membranes as shown in FIGS. 15A and 15B. These membranes are preferably coated with substrates (e.g., proteins) that promote cell adhesion such as but not limited to gelatin, fibronectin, laminin, or Matrigel (i.e., a gelatinous protein mixture secreted by mouse tumor cells, commercially available from BD Biosciences). Combinations of these substrates may also be employed. The Examples demonstrate the use of culture vessels having silicone rubber bottom membranes. Importantly, the use of oxygen-permeable membranes such as those of the Examples eliminates the need for stirred or perfused culture systems such as those used in the prior art. (Bauwens et al., Biotechnol Bioengin, 90(4):453-461, 2005).

The culture conditions for the low oxygen partial pressure exposure (i.e., in order to reduce pluripotent stem cell number and/or function) may vary depending on the nature of the differentiated cell population. In some instances, the culture may be supplemented with growth factors such as cytokines, interleukins or small molecules. In other instances, the culture does not comprise any exogenous growth factors. In some embodiments, the culture conditions used for the low oxygen partial pressure exposure are similar or identical to those used to culture primary cells of the same lineage(s). For example, the culture conditions for a differentiated cell population that comprises neural cells may be similar or identical to that used to culture (e.g., maintain) freshly explanted neural cells from in vivo sources. In some embodiments, the culture conditions used for low oxygen partial pressure exposure are similar or identical to the differentiation culture conditions used to generate the differentiated cell population in the first instance. In some embodiments relating to differentiated cell populations that comprise cardiomyocytes, the differentiated cell population may be cultured in insulin, transferring and selenium containing medium (ITS). In some instances, such medium is serum-free. In some instances, such medium comprises serum.

The differentiated cell population is typically harvested following low oxygen exposure (for the purpose of reducing pluripotent stem cell number). Thus, in some instances, this population is referred to as being "harvested" or as being the "harvested differentiated cell population". Once harvested, the population may be further manipulated or it may used in vitro or in vivo as described herein. Similarly, even if the population is not harvested and/or further manipulated, it may be referred to as the "cultured differentiated cell population" in order to distinguish it from its starting differentiated cell population (i.e., the differentiated cell population prior to low oxygen exposure for the purpose of reducing pluripotent stem cell numbers).

Assay for Pluripotent Stem Cells

The number of pluripotent stem cells in the cell population may be monitored prior to, during and/or after low oxygen exposure. Pluripotent stem cells may be monitored by in vivo (preferably non-human) assays and/or in vitro assays. In vivo assays may involve administration of a cell population into a non-human subject in order to determine if teratoma-causing cells are present. A well-known assay is the injection of cells into an immunocompromised animal, such as an immunocompromised mouse. Immunocompromised mice such as SCID mice are a suitable recipient in these assays, although it is to be understood that other mouse immunocompromised or wild type mouse strains may also be used. In other instances, immunocompromised or wild type preferably non-human animals other than mice can be used as recipients. In this assay, the site of injection is observed over a period of time for the appearance of a tumor. The time it takes for tumors to develop and be observable is dependent on the number of administered pluripotent stem cells and the site of injection. For example, a population having more pluripotent stem cells will form an observable tumor faster than will a population having few pluripotent stem cells. As shown in the Examples, populations exposed to low oxygen conditions exhibited delayed visual appearance of tumors at the site of injection as compared to untreated controls, indicating that the number of pluripotent stem cells in the treated population was reduced compared to the untreated control.

An exemplary protocol for assaying pluripotent stem cells by teratoma formation is described by Keller et al. Genes Dev 19:1129-1155, 2005; Spagnoli et al. Curr Opin Genet Different 16:469-475, 2006. Briefly, a cell population is injected subcutaneously or intramuscularly into preferably an immunocompromised mouse. The administration route is preferably one that maintains the administered cells locally in order to ensure easy access, observation and harvest of any resulting tumor mass. The number of cells to be administered will depend upon the population being tested and the expected frequency of pluripotent stem cells in the population. If one aim of the assay is to determine the number or frequency of the stem cells in the population, a limiting dilution assay may be carried out in which a range of cell numbers are injected. Another measure of stem cell number may be obtained by performing a time course of tumor development for a number of populations having known stem cell number, thereby generating a standard curve, and then comparing the readout from the test population (or various aliquots of the test population) to the standard curve. A biopsy of any resulting tumor may also be performed to confirm the pluripotent nature of the teratoma-causing cells. The presence of endodermal, mesodermal and ectodermal lineages can be determined via immunohistochemical staining, microscopy (e.g., transmission electron microscopy, TEM), Northern blot analysis, reverse transcriptase polymerase chain reaction (RT-PCR), real-time PCR, RNA fluorescence in situ hybridization (FISH), or rapid amplification of cDNA ends (RACE) techniques. Further reference can be made to *Human Embryonic Stem Cells: The Practical Handbook*, Eds. Sullivan, Cowan and Eggan, Harvard University, John Wiley & Sons (Publishers), 2007.

Additionally or alternatively, the presence of pluripotent stem cells may be determined in vitro by detecting mRNA and/or protein expression of stem cell markers. Stem cell markers are genes that are preferentially (and in some instances exclusively) expressed by pluripotent stem cells. Typically, the markers are chosen such that they are not expressed by non-stem cells in the differentiated cell population. Thus, the presence and number of pluripotent stem cells may be determined by detecting or measuring mRNA or protein expression levels of these markers. These markers include Oct4 (also known as POU5F1), Sox2, Nanog, SSEA-1 (for mouse), SSEA-4 (for human), Stat3, Hesx1, Zic3, Tra-1-60, Tra-1-80, alkaline phosphatase, Klf4, Lin28, and hTERT. In some important embodiments, the marker is Oct4.

mRNA levels can be monitored using Northern blot analysis, reverse transcriptase polymerase chain reaction (RT-PCR), real-time PCR, RNA fluorescence in situ hybridization (FISH), or rapid amplification of cDNA ends (RACE) techniques. In some instances, real time and reverse transcriptase PCR are combined. PCR primers and/or probes specific for Oct4 and other stem cell markers are known in the art and reference may be made to Powers et al. Biotechnol Bioeng 101(2):241-54 (2008) for exemplary sequences. Protein levels may be monitored using Western analysis, enzyme assay, immunocytochemistry, flow cytometry and other techniques. Antibodies specific for pluripotency proteins such as Oct4 are known in the art and commercially available from sources such as R&D Systems (Minneapolis, Minn.).

As discussed herein, the invention contemplates reducing the pluripotent stem cell content of a cell population using the low oxygen methods provided herein by 2-fold, more preferably by 5-fold, more preferably by 10-fold, and even more preferably by 20-fold. In still other instances, the pluripotent stem cell content of the cell population may be reduced by 50-fold, 75-fold, 100-fold, 125-fold, or 150-fold, or more. As an example, a 10-fold decrease in stem cell numbers may be indicated by an Oct4 mRNA expression level that is 10-fold lower than the expression level prior to low oxygen exposure. Fold decreases can be measured in vivo by comparing the time course of a test population with that of control populations having known numbers of pluripotent stem cells, as described herein.

Thus, the invention contemplates monitoring stem cell function in a differentiated cell population during low oxygen exposure. As an example, the differentiated cell population is exposed to low oxygen culture for a period of time and aliquots are taken from the population at various times and tested for teratoma activity and/or mRNA or protein expression. Such a time course assay may reveal the duration of low oxygen exposure required to eliminate pluripotent stem cells. In this way, the differentiated cell population need not be cultured at low oxygen unnecessarily beyond the point at which no pluripotent stem cells exist in the population. It is expected that any cell population intended for in vivo use in humans will be tested in this manner prior to actual administration into a subject.

Differentiation Protocols

It is to be understood that the invention contemplates reducing pluripotent stem cell numbers in any differentiated population regardless of the type of differentiated cell lineage and/or the manner of differentiating. Mesodermal cells and progenitors (or tissues) include bone, muscle such as cardiac muscle, skeletal muscle and smooth muscle (e.g., of the gut), connective tissue such as the dermis and cartilage, kidneys, the urinoogenital system, blood (or hematopoietic), heart and vasculature. Endodermal cells and progenitors (or tissues) include epithelial cells such as those lining the digestive tube, liver, pancreas including the beta cells in islets of Langerhans, trachea, bronchi, alveoli, urinary bladder, urethra, thyroid and thymus. Ectodermal cells and progenitors (or tissues) include nerve cells (and nervous tissues) such as astrocytes, neurons including spinal motor neurons, glia, skin, hair, and epidermis.

Various methods for differentiating pluripotent stem cells are known in the art. These include differentiation protocols described in U.S. Pat. No. 7,326,572 (endoderm differentiation), U.S. Pat. No. 7,282,366 (hepatocyte differentiation), U.S. Pat. No. 7,250,294 (neural differentiation), U.S. Pat. No. 7,033,831 (islet cell differentiation), and in published PCT application WO2008/156708.

Differentiation of ES cells may be achieved via induction of embryoid body (EB) formation. As an example, differentiation towards the cardiomyocyte lineage can be achieved using EB formation. Briefly, this method involves dispersing ES cells into a single cell suspension of ES cell medium lacking LIF, followed by culture in hanging drops for 2 days. EB generation via the hanging drop method may employ DMEM with 10% FBS either in the presence or absence of ascorbic acid. The hanging drop method is preferred to the extent that it provides better control and uniformity in size and shape. After 2 days of culture, the EBs are transferred into a culture vessel (e.g., a flask, a plate, or a well (e.g., from a multi-well dish)). Preferably, the culture vessel is coated with a substrate that promotes cell adhesion such as but not limited to gelatin, fibronectin, or laminin. In some embodiments, combinations of these substrates may be used. For example, in some instances it may be useful to coat the vessel with fibronectin followed by gelatin. The EBs are allowed to differentiate for 2, 3, 4, or more days with daily medium changes, followed by a change to a serum-free medium supplemented with insulin, transferrin and selenium (ITS; see Methods and Materials in the Examples section below) with or without 0.2 mM ascorbic acid. The cells may be cultured for an additional 5, 6, 7 or more days in these latter conditions. Differentiation of human ES cells can be achieved using the same hanging drop method procedure and the same medium as used for maintenance of undifferentiated ES cells except that bFGF is omitted.

Although many aspects and embodiments of the invention are described in the context of cardiomyocytes, it is to be understood that the invention is not so limited and that other mesodermal, endodermal and ectodermal cell types, including progenitors and more differentiated cells such as terminally differentiated end stage cells, may be similarly be treated to low oxygen conditions in order to reduce pluripotent stem cell number.

A variety of differentiation factors that can act on pluripotent stem cells and their precursor progeny are known in the art. For example, members of the BMP family of factors have been used to differentiate stem cells such as ES cells. These include the use of BMP-4 and BMP-7 to generate endoderm-like differentiation. (Xu et al. Nat Biotechnol 20:1261-1264, 2002; Pera et al. J Cell Sci 117:1269-1280, 2004.) Activin A can be used to differentiate pluripotent stem cells such as ES cells into definitive endoderm using monolayers or three dimensional (e.g., EB) culture systems. (D'Amour et al. Nat Biotechnol 23:1534-1541, 2005.)

Nervous system cells have been observed as a result of culture with epidermal growth factor and fibroblast growth factor (resulting in the generation of neurospheres that comprise neural stem cells), subsequent removal of these factors (resulting in the generation of astrocyte-like cells) or supplementation with nerve growth factor (resulting in the generation of neurons and glial cells). (Kim et al. Nature 418:50-6, 2002; Lee et al. Nat Biotechnol 18:675-9, 2000.) Dopaminergic neurons, useful in Parkinson's disease, may be formed through culture or contact with FGF20 and FGF2. Bjorklund et al. (PNAS 2002, 99:2344-2349) provides additional methods for differentiating ES cells into dopaminergic neurons.

Hepatic cell differentiation may be induced through contact and/or culture with an insulin, dexamethasone, and collagen type I (via EB formation) combination; a sodium butyrate and DMSO combination; an FGF4, HGF and collagen type I combination; an aFGF, HGF, oncostatin M, dexamethasone and collagen type I combination; and a bFGF, variant HGF, DMSO and dexamethasone combination in the presence of poly-amino-urethane coated non-woven polytetrafluoroethylene fabric. (Shirahashi et al. Cell Transplant 13:197-211, 2004; Rambhatla et al. Cell Transplant 12:1-11, 2003; Schwartz et al. Stem Cells Dev 14:643-655, 2005; Baharvand et al. Int J Dev Biol 50:645-652, 2006; Soto-Gutierrez et al. Cell Transplant 15:335-341, 2006.) Hepatic differentiation may also occur spontaneously. (Lavon et al. Differentiation 72:230-238, 2004.)

Pancreatic differentiation, including differentiation towards beta-islet cells, can be induced using Activin A, retinoic acid, FGF2 and FGF10, betacellulin, HGF, Exendin 4, DKK1 and DKK3. (Gu et al. Mech Dev 120:35-43, 2003; Grapin-Botton et al. Trends Genet 16:124-130, 2000; D'Amour et al. Nat Biotechnol 23:1534-1541, 2005a; D'Amour et al. published US application US2005-0266554A1.)

Endothelial differentiation may be induced in the presence of ECM proteins such as collagen type IV, optionally in the presence of VEGF and bFGF. (Gerecht-Nir et al. Lab Invest 83:1811-1820, 2003.)

Further reference may be made to published PCT application WO2009/007852 for a review of various differentiative procedures known in the art and applicable to the differentiation of the immature and precursor cells of the invention. Such teachings, and in particular those found on pages 57-61 (under the subheading "Cell Differentiation") of WO2009/007852, are incorporated by reference herein. Still other references include West and Daley, 2004, Curr Opin Cell Biol 16:688-692; U.S. Pat. No. 6,534,052 B1; Kehat and Gepstein, 2003, 8:229-236; Nir et al., 2003, 58:313-323; and U.S. Pat. Nos. 6,613,568 and 6,833,269.

Cardiomyocytes, Cardiomyocyte Progenitor Cells, and Other Differentiated Cells

In various aspects of the invention, the differentiated cell population comprises cardiomyocytes and/or cardiomyocyte progenitor cells. As used herein, cardiomyocyte progenitors are cells that have committed to the cardiomyocyte lineage but which still exhibit substantial proliferative and optionally differentiative capacity. One population of cardiomyocyte progenitors has an isl1+/Nkx2.5/flk-1+ phenotype. This population can be counted or extracted using flow cytometry and sorting. Another population of cardiomyocyte progenitors has a brachyury+/flk-1+ phenotype.

Flow cytometry can be used to detect and count cardiomyocytes and their progenitors using one or more cardiac lineage markers. The cardiomyocyte lineage marker preferably is specific to the cardiomyocyte lineage (i.e., expressed only in cells committed to the cardiomyocyte lineage). Non-specific markers may also be used in some instances. Typical cardiomyocyte lineage markers include but are not limited to brachyury, nkx2.5, cardiac troponin I, or α-myosin heavy chain (α-MHC), gata-4, atrial natriuretic protein (ANP), myosin light chain (MLC)-2v, β-myosin heavy chain (β-MHC), and connexin 43. MF-20, an anti-sarcomeric myosin heavy chain antibody (commercially available from DBHB, Iowa City, Iowa) can also be used to identify cardiomyocyte committed cells. It is to be understood that these methods can be readily applied to any other marker, provided a probe for such marker is available.

Cardiomyocyte and/or cardiomyocyte progenitor presence in the cultures of the invention may also be detected according to mRNA expression profiles. For example, the presence of these cells may be determined by the presence of brachyury, nkx2.5, cardiac troponin I, or α-myosin heavy chain (α-MHC), gata-4, atrial natriuretic protein (ANP), myosin light chain (MLC)-2v, β-myosin heavy chain (β-MHC), and connexin 43 mRNA transcripts within cultured cell populations. Methods for detecting mRNA transcripts from differentiated cell populations (including cultured populations) are known in the art.

Endoderm progenitors that contribute to pancreatic development may be characterized by their gene expression profiles also. Stage 1 (definitive endoderm (DE) progenitor cells) express SOX17, CER, FOXA2, and CXCR4 and cells transitioning from ES cells to DE cells express BRA, FDF4, WNT3 and NCAD. Stage 2 endoderm progenitors express HNF1B and HNF4A. Stage 3 endoderm progenitors express PDX1, HNF6 and HLXB9. Stage 4 endoderm progenitors express NKX6-1, NGN3, PAX4 and NKX2-2. And finally stage 5 endoderm progenitors express INS, CGC, GHRL, SST and PPY.

Negative and/or Positive Selection Steps

The invention further contemplates that negative and/or positive selection steps may be used in addition to low oxygen exposure to reduce the number of pluripotent stem cells in a differentiated cell population. The selection steps, whether negative or positive, may be performed prior to and/or after low oxygen exposure. Selection methods may be based on, for example, cell surface phenotype, cell size and/or granularity, cell cycle status, reporter gene expression (e.g., a detectable marker, such as GFP, tagged to a protein under the control of mesoderm or endoderm-associated transcription factor(s)), and the like. These selection methods may be applied to cells harvested at any stage of culture. These methods are known in the art and the invention is not to be limited in this regard.

As used herein, a negative selection step is one that selects for, and preferably removes, pluripotent stem cells in order to reduce their numbers. Conversely, a positive selection step is one that selects for, and preferably retains, the differentiated cells of interest.

Negative and positive selection may be performed based on any criteria known to distinguish pluripotent stem cells from differentiated cells. In some instances, the selection is performed based on cell surface markers that are preferentially (or exclusively) expressed by one cell type but not the other. These markers can therefore be those expressed by pluripotent stem cells or they may be those expressed by differentiated cells. It will be understood that the markers expressed by differentiated cells will vary based on the nature of the differentiated cells (e.g., cardiomyocyte markers will differ from hepatic cell markers, etc.), and in some instances on the developmental stage of the differentiated cells. For example, markers for pluripotent stem cells include SSEA-4, TRA-60, CD9, and Oct4. A marker for cardiomyocytes is ALCAM (CD166). Selection, and thus separation, based on cell surface markers can be effected using antibodies to the cell surface markers of choice combined with fluorescence activated cell sorting (FACS), panning, magnetic bead separation, and the like. Selection, and thus separation, based on transcription factor expression can be effected using temporally controlled suicide genes or reporter genes, the products of which can be observed and used as a physical sorting parameter (e.g., GFP expression).

Physical parameters that can be used to separate pluripotent stem cells from differentiated cells include buoyant density (e.g., using a Ficoll or Percoll gradient), size, granularity, and the like.

In Vivo Uses

The differentiated cell populations of the invention may be used in a variety of in vivo methods including but not limited to therapeutic or cosmetic applications. The differentiated cell populations can be used in transplant settings in the treatment or prevention of various conditions including but not limited to Parkinson's disease (dopaminergic neurons), Alzheimer's disease (neural precursors), Huntington's disease (GABAergic neurons), blood disorders such as leukemia, lymphoma myeloma and anemia (hematopoietic cells), side-effects of radiation e.g., in transplant patients (hematopoietic precursors), cardiovascular disease, myocardial infarction, ischemic cardiac tissue or heart-failure (partially- or fully-differentiated cardiomyocytes), muscular dystrophy (skeletal muscle cells), liver cirrhosis or failure (hepatocytes), chronic hepatitis (hepatocytes), diabetes including type I diabetes (insulin-producing cells such as islet cells), ischemic brain damage (neurons), spinal cord injury (glial progenitor cells and motor neurons), amyotrophic lateral sclerosis (ALS) (motor neurons), orthopedic tissue injury (osteoblasts), kidney disease (kidney cells), corneal scarring (corneal stem cells), cartilage damage (chondrocytes), bone damage (osteogenic cells including osteocytes), osteoarthritis (chondrocytes), myelination disorders such as Pelizaeus-Merzbacher disease, multiple sclerosis, adenoleukodystrophies, neuritis and neuropathies (oligodendrocytes), and hair loss.

The differentiated cell populations may be provided as pharmaceutical compositions that are sterile and appropriate for in vivo use, optionally together with a pharmaceutically acceptable carrier. As used herein, a pharmaceutically-acceptable carrier means a non-toxic material that does not interfere with the effectiveness of the biological activity of the active ingredients. Pharmaceutically acceptable carriers include diluents, fillers, salts, buffers, stabilizers, solubilizers and other materials which are well-known in the art. Such preparations may routinely contain salt, buffering agents, preservatives, compatible carriers, and optionally other therapeutic agents. The differentiated cell population may be formulated for local or systemic administration including as part of an implant.

The cells may be used alone or together with another agent, whether active or inactive, including but not limited to a scaffold, a matrix, and the like. These cells may further be included in a kit that additionally comprises at a minimum instructions for use of the cells, and optionally comprises one or more other agents whether active or inactive. The cells may be provided as a frozen aliquot of cells, a culture of cells, or a liquid suspension of cells.

The differentiated cells may be administered in numbers effective to produce a desired result, including but not limited to a short-term or long-term therapeutic result. Such result may include an improvement in or complete eradication of symptoms associated with a particular condition. The cell numbers to be administered will depend on a number of factors including the weight and age of the subject, the type of condition being treated, the desired effect (e.g., short-term or long-term), and the like. Some treatments therefore may require as few as $10^3$ cells, while others may require $10^4$, $10^5$, $10^6$, $10^7$, $10^8$, $10^9$ or more cells.

In Vitro Uses

The differentiated cell populations produced according to the invention may also be studied for gene expression profiles and responses to various external stimuli in order to understand differentiation more fully and independently of effects at the pluripotent stem cell level or stage since the population would be essentially devoid of such cells.

The invention further provides methods for screening and/or identifying agents (or compounds, as the terms are used interchangeably herein) being used or to be used clinically. These assays may measure the therapeutic efficacy and/or toxicity of the candidate agent, among other things. The readouts from such in vitro assays are correlative of the in vivo toxicity or efficacy such agents would exhibit in subjects. Thus, the effect of the agent on the differentiated cells generated according to the invention in vitro is a form of surrogate marker or readout for how the agent will function in vivo in a subject. The agents to be tested include those used clinically as well as experimental agents. In some more common embodiments, such testing will focus on the toxicity of agents including drugs in particular differentiated progeny. Accordingly, in these assays, the readout would be cell death (or conversely cell viability). These in vitro assays may employ suspensions of differentiated cells, adherent populations of differentiated cells, or three dimensional structures comprised of differentiated cells (e.g., in vitro organ tissues, matrices and architectures).

Drugs that can be tested according to these methods particularly for whether they are toxic to cells include but are not limited to adrenergic agent; adrenocortical steroid; adrenocortical suppressant; aldosterone antagonist; anabolic; analeptic; analgesic; androgen; anesthesia, adjunct to; anesthetic; anorectic; anterior pituitary suppressant; anti-acne agent; anti-adrenergic; anti-allergic; anti-androgen; antianemic; anti-anginal; anti-arthritic; anti-asthmatic; anti-atherosclerotic; anticholelithic; anticholelithogenic; anticholinergic; anticoagulant; anticoccidal; anticonvulsant; antidepressant; antidiabetic; antidiarrheal; antidiuretic; antiemetic; anti-epileptic; anti-estrogen; antifibrinolytic; antiglaucoma agent; antihemophilic; antihemorrhagic; antihistamine; antihyperlipidemia; antihyperlipoproteinemic; antihypertensive; antihypotensive; anti-inflammatory; antikeratinizing agent; antimigraine; antimitotic; antimycotic, antinauseant, antineoplastic, antineutropenic, antiparkinsonian; antiperistaltic, antipneumocystic; antiproliferative; antiprostatic hypertrophy; antipruritic; antipsychotic; antirheumatic; antiseborrheic; antisecretory; antispasmodic; antithrombotic; antitus sive; anti-ulcerative; anti-urolithic; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; immunomodulator; immunoregulator; immunostimulant; immunosuppressant; impotence therapy adjunct; keratolytic; LHRH agonist; liver disorder treatment; luteolysin; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; progestin; prostaglandin; prostate growth inhibitor; prothyrotropin; psychotropic; pulmonary surface; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; symptomatic multiple sclerosis; thyroid hormone; thyroid inhibitor; thyromimetic; tranquilizer; amyotrophic lateral sclerosis agent; cerebral ischemia agent; Paget's disease agent; unstable angina agent; uricosuric; vasoconstrictor; vasodilator; wound healing agent; xanthine oxidase inhibitor. Those of ordinary skill in the art will know or be able to identify agents that fall within any of these categories, particularly with reference to the Physician's Desk Reference.

The following Examples are provided to illustrate specific instances of the practice of the present invention and are not intended to limit the scope of the invention. As will be apparent to one of ordinary skill in the art, the present invention will find application in a variety of compositions and methods.

EXAMPLES

Methods and Materials
Undifferentiated Mouse Embryonic Stem Cell (mESC) and Mouse Induced Pluripotent Stem Cell (miPSC) Culture.

Undifferentiated R1 mESC and miPSC, both with an inserted GFP coding sequence driven by an inserted Oct4 promoter (Oct4-GFP mESC) [1] (generously donated by Professor Douglas Melton of Harvard University, Cambridge, Mass., USA), and R1 mESC with a homozygous HIF-1α gene knockout (HIF-1α$^{-/-}$ mESC) [2] (generously donated by Professor Peter Carmeliet of Katholieke Universiteit Leuven, Leuven, Belgium) were propagated as described previously [3] in Dulbecco's modified eagles medium (DMEM; SCRR-2010; American Type Culture Collection (ATCC), Manassas, Va., USA) supplemented with 10% fetal bovine serum (FBS; SCRR 30-2020; ATCC), 1× L-alanyl-L-glutamine (SCRR 20-2115; ATCC), 1× penicillin streptomycin (P/S; 15070; Invitrogen, Carlsbad, Calif., USA), 1× MEM non-essential amino acids (SCRR 20-2116; ATCC), 100 µM 2-mercaptoethanol (M7522; Sigma-Aldrich; St. Louis, Mo., USA), and $10^3$ units/mL leukemia inhibitory factor (LIF2005; Millipore, Billerica, Mass., USA). Briefly, cells were grown in 25 cm$^2$ cell culture flasks (Becton Dickinson) using 4 mL of medium (Table 1) exchanged daily. Cells were detached with 0.25% trypsin every two days and placed in a new culture flask at a density of $1.2 \times 10^4$ cell/cm$^2$.

Gas Phase pO$_2$ Control.
Cell culture vessels were placed inside polystyrene chambers (MIC-101, Billups-Rothenburg, Del Mar, Calif.) contained within a standard incubator (OWJ2720A, Queue Systems, Parkersburg, W. Va.) maintained at 37° C. An open dish of deionized water in each chamber provided humidification. pO$_{2gas}$ was maintained by flowing premixed gas containing 5% CO$_2$ and 20%, 5%, or 1% O$_2$ with a balance of N$_2$ (certified medical gas from Airgas, Hingham, Mass., USA), which corresponded, under humidified conditions, to 142, 36, and 7 mmHg pO$_{2gas}$ inside chambers maintained at 37° C., as described previously [3]. The flow rate of this gas to the chambers was 2 L/min for 15 min for an initial purge following closure of the chamber (after cell medium exchange or passage); and was 30 mL/min at all other times.

Differentiation of mESC and miPSC.
mESC and miPSC were differentiated as previously described [3]. In brief, embryoid bodies (EBs) were formed with 500 cells per 20-µL in propagation medium without LIF in hanging drops. Detached undifferentiated mES cells were centrifuged, supernatant medium removed, resuspended in medium without LIF (Table 1), and diluted to 25,000 membrane-intact cells/ml. Single 20-µl drops of this cell suspension were placed on the inside surface of the lids of 10×10 cm Petri dishes (Becton Dickinson) using an 8-channel pipette. The lids were inverted and placed onto dish bottoms filled with 15 ml of pre-warmed (37° C.) solution containing 75% DPBS, 25% water, and 0.002% (w/v) type A gelatin. After 2 days, 30 EBs were transferred per well of fibronectin-coated (F1141; Sigma) 24-well silicone rubber plates filled with 2 mL of propagation medium without LIF. After 3 additional days, medium was replaced with 2.5 mL of 50% DMEM (90-133-PB; Mediatech, Manassas, Va., USA) and 50% Ham's F-12 (10-080-CV; Mediatech) supplemented with 0.75% (w/v) sodium bicarbonate (25-035-CI; Mediatech), 9 mM glucose (G8769; Sigma-Aldrich), 5 µg/mL human insulin (19278; Sigma-Aldrich), 50 µg/mL holo transferring (T1283; Sigma-Aldrich), 31.2 nM sodium selenite (S9133; Sigma-Aldrich), and 1× P/S (see Table 2). Cells were differentiated for a total of ten days. In some conditions in Table 3, 0.2 mM ascorbic acid (A4034; Sigma-Aldrich) was also included. This protocol produces a final population of approximately 10% and 30% cardiomyocytes at 142 and 7 mmHg, respectively.

Extended Culture of Differentiated mESC and miPSC.
After the ten day differentiation protocol, cells were subjected to extended culture for up to 80 extra days. In some experiments, the pO$_{2gas}$ was identical to the pO$_{2gas}$ during differentiation, while in others the pO$_{2gas}$ was changed. Cell samples were acquired by detachment with a 5 minute incubation of 0.25% trypsin (25-053-CI; Mediatech) at 37° C.

Silicone Rubber Membrane-Based Plate.
Differentiation and extended culture was performed on custom-made silicone rubber plates, having high oxygen permeability, as described previously [3]. In brief, the bottoms of 24-well polystyrene plates (353047; Becton Dickinson) were replaced with silicone rubber sheets (nonreinforced vulcanized gloss/gloss 0.005" thick; Specialty Manufacturing, Saginaw, Mich., USA) and sterilized by filling with 70% (v/v) ethanol (111000200; Pharmco-AAPER, Brookfield, Conn., USA) in water for 1 hr and drying overnight under a germicidal UV lamp in a biological safety cabinet (SterilGARD III Advance; The Baker Company, Sanford, Mass., USA). In use, the plated sat on top of a 150×15 mm Petri dish (35384-326; VWR, West Chester, Pa., USA) such that only the corners of the plates was supported by the Petri dish and the silicone rubber membrane was exposed directly to the gas phase. By using silicone rubber membranes, pO$_{2cell}$ at the cell-membrane interface was maintained equal to pO$_{2gas}$, and rapid equilibration of pO$_{2cell}$ after a change in pO$_{2gas}$ was achieved. Cell attachment was achieved by incubating silicone rubber membranes at 37° C. with, for triESC, 2 µg/mL fibronectin (F1141; Sigma-Aldrich) in PBS (21-040; Mediatech) for 24 hr or, for human embryonic stem cells (hESC), Matrigel (354234, Becton Dickinson) diluted 1:20 in serum-free medium for 1 hr.

Flow Cytometric Analysis of Oct4-GFP Expression.
Medium was removed from the wells of the 24-well silicone rubber membrane-based culture dish, the cells were washed with PBS, and 200 µl of trypsin solution was added to each well. After 5-min incubation at 37° C., 800 µl of ES cell differentiation medium was added to each well. The contents of the well were vigorously pipetted using a 1 ml pipette to dislodge and disperse the cells and were then transferred to a 1 ml tube. Detached cell Oct4-GFP expression was measured with a flow cytometer (FACScan; Becton Dickinson). A negative control was prepared using R1 mESC without the Oct4-GFP reporter differentiated under the same conditions as the Oct4-GFP cells and gating set so that all cells were counted as negative for Oct4-GFP. The fraction of cells expressing Oct4-GFP (Oct4-GFP+) was measured with flow cytometry and calculated as the number of cells above this threshold divided by the number of cells in the entire population at each specific measurement time and condition.

Real-Time Polymerase Chain Reaction (PCR).

Total RNA was isolated using the RNeasy Kit (74104, Qiagen, Valencia, Calif.) and RNase-Free DNase Set (79254, Qiagen), cDNA was synthesized using High Capacity cDNA Reverse Transcription Kit (4368814, Applied Biosystems, Foster City, Calif.), and real-time polymerase chain reaction (PCR) was performed on a Fast Real-Time PCR System (7900HT, Applied Biosystems), using Power SYBR Green PCR Master Mix (4367659, Applied Biosystems). 28S ribosomal RNA (rRNA) was used as an endogenous control. Primer sequences for 28S rRNA, Oct4 (mouse), Nanog (mouse), Nestin, and Nkx2.5 have been previously reported [4]. The following additional primers sequences were used (in order of forward and reverse primer and 5' to 3'): Brachyury T TCCCGGTGCTGAAGGTAAAT (SEQ ID NO:1) and CCGTCACGAAGTCCAGCAA (SEQ ID NO:2), Foxa2 TCAAGGCCTACGAACAGGTCAT (SEQ ID NO:3) and GCCCGCTTTGTTCGTGACT (SEQ ID NO:4), cTnT AGATGCTGAAGAAGGTCCAGTAGAG (SEQ ID NO:5) and CACCAAGTTGGGCATGAAGA (SEQ ID NO:6), cardiac-α-Actin GCTTCCGCTGTCCA-GAGACT (SEQ ID NO:7) and TGCCAGCAGATTCCAT-ACCA (SEQ ID NO:8), OCT4 (human) TGGGCTCGA-GAAGGATGTG (SEQ ID NO:9) and GCATAGTCGCTGCTTGATCG (SEQ ID NO:10), and NANOG (human) GCAAATGTCTTCTGCTGAGATGC (SEQ ID NO:11) and CCATGGAGGAGGGAAGAGGA (SEQ ID NO:12). A standard calibration curve was constructed using pooled cDNA from all conditions, serial diluted.

Cell Processing for Nuclei Counts and Immunostaining.

Medium was removed from each well, attached cells were washed with DPBS, and 200 µl of trypsin solution was added. After 5 min at 37° C., 800 µl of differentiation medium was added, and the contents were vigorously pipetted up and down using a 1-ml pipette to dislodge and disperse the cells, which were transferred to a 1 ml tube and allowed to settle for 2 min. The bottom 50 which contained any remaining large clumps of cells and extra-cellular matrix, was removed and discarded (or saved for later analysis). The cell sample was mixed by vortexing, and an aliquot saved for nuclei counting. The remaining cell sample was centrifuged, and the supernatant, discarded. Cells were resuspended in 750 µl DPBS, 250 µl of 4% (w/v) paraformaldehyde (Alfa Aesar, Ward Hill, Mass.) in DPBS was added to fix the cells, and each sample was incubated for 20 min at room temperature. Samples were then centrifuged, supernatant removed, and 1 ml of DPBS added. Samples of nuclei and of fixed cells were stored at 4° C. prior to analysis.

Cell Enumeration.

Detached cells were lysed by vigorous vortexing in 1% Triton X-100 (T-9284; Sigma-Aldrich) and 0.1 M citric acid (0627; Mallinckrodt Specialty Chemicals Co., Paris, Ky., USA) in deionized water to liberate nuclei. Nuclei were stained with Guava ViaCount (4000-0041; Millipore) and counted using a Guava PCA flow cytometer (Millipore), as previous described [3].

Cell Implantation into Mice.

SCID mice and 43-56 day old female nude mice (Charles River Laboratories International, Wilmington, Mass., USA) were housed and cared for at MIT under the supervision of the committee on animal care, and experiments were performed using an approved protocol (#1007-082-10). The protocol for implanting cells was based on one designed to be a reliable animal model for biosafety testing of stem cell products. Using this protocol, implantation of only two ES cells was sufficient to form detectable tumors [5]. $10^5$ cells (for mESC and miPSC) and $10^6$ cells (for hESC) in 200 µl of 50% Matrigel (354234; BD Biosciences, Bedford, Mass., USA) and 50% serum-free media were injected subcutaneously into the lower left flank of isoflurane-anaesthetized mice using a 23 G needle in a laminar-flow hood. Mice were observed every 3-4 days for the appearance of masses under the skin.

Histology.

Tumors were excised from sacrificed mice, fixed overnight in 4% paraformaldehyde (36606; Alfa Aesar, Ward Hill, Mass., USA) in PBS, paraffin embedded, sectioned, and stained with hematoxylin and eosin (H&E) at the Division of Comparative Medicine at MIT.

Flow Activated Cell Sorting (FACS).

Before sorting, Oct4-GFP mESC underwent 10 days differentiation, 20 days extended culture, and were detached trypsin. Cells were then either sorted with an Aria 2 FACS (Becton Dickinson) into Oct4-GFP+ and Oct4-GFP− populations or sorted based on expression of the mESC surface marker SSEA-1. For SSEA-1 sorting, cells were treated with a phycoerythrin (PE)-conjugated anti-SSEA-1 antibody (12-8813; eBioscience, San Diego, Calif., USA) before sorting into SSEA-1+ and SSEA-1− populations.

Flow Cytometric Analysis of Immunostained Cells.

The fraction of Nestin+ and MF-20+ cells was measured with flow cytometry, as previously described [3]. In brief, detached cells were fixed in 1% (w/v) paraformaldehyde in PBS for 20 min. $3 \times 10^5$ fixed cells were incubated 10 min in 0.5% (w/v) saponin (S-4521; Sigma-Aldrich) in PBS to permeabilize cell membranes, and then incubated in 2% (v/v) FBS in PBS for 30 min to block. Cells were incubated with primary anti-Nestin (MAB2736; R&D Systems, Minneapolis, Minn., USA) diluted 1:50 or anti-sarcomeric myosin heavy chain (MF-20; MF-20 supernatant; Developmental Studies Hybridoma Bank (DSHB), Iowa City, Iowa, USA) diluted 1:10 antibody for 1 hour, washed 1×, and incubated with secondary goat anti-mouse PE-conjugated antibody (Jackson ImmunoResearch, West Grove, Pa.) diluted 1:250 in 2% FBS in the dark. Stained cells were washed thrice with 2% FBS, and fluorescence intensity data were acquired using the Guava PCA flow cytometer with the Express software module.

Immunocytochemistry.

Cells attached to silicone rubber were fixed in 4% (w/v) paraformaldehyde in PBS for 20 min and then permeabilized and blocked with a 45 min incubation in 3% donkey serum (DS; D9663; Sigma-Aldrich) and 0.1% Triton X-100 in PBS. Cells were then incubated overnight at 4° C. with primary anti-Oct4 (sc-9081; Santa Cruz Biotechnology, Santa Cruz, Calif., USA) diluted 1:100, anti-Nanog (IHC-00205; Bethyl Laboratories, Montogomery, Tex., USA) diluted 1:100, anti-SSEA-1 (MC-480; DSHB) diluted 1:10, anti-Foxa2 (sc-6554; Santa Cruz Biotechnology) diluted 1:200, anti-Nestin diluted 1:50, or anti-cardiac troponin T (cTnT; MS-295-P1; NeoMarkers, Fremont, Calif., USA) diluted 1:50 antibody in 3% DS, washed 1×, and incubated with secondary donkey Alexa Fluor 488 (green) or 594 (red) antibodies (Invitrogen) against the appropriate species diluted 1:250 for 2 hr in the dark. DNA was stained with a 10 min incubation with 1 µg/mL 4′,6-diamidino-2-phenylindole (DAPI; 32670, Sigma-Aldrich) in the dark. Stained cells were then washed thrice with 3% DS and images acquired with an Axiovert 200 fluorescence microscope (Carl Zeiss, Oberkochen, Germany).

Differentiation of hESC.

CyT49 hESC (generously provided by ViaCyte, Inc, San Diego, Calif., USA) were plated on Matrigel-coated silicone rubber plates at $1.5 \times 10^5$ cells cm$^{-1}$, propagated 4 days in self-renewal media, and then switched to DMEM/F12 (15-090-CV; Mediatech) with 10% Knockout™ serum replacement (A1099202; Invitrogen) for up to 90 days.

Statistics.

Statistical analysis was performed using unpaired t-tests, with significant results requiring $p<0.05$. Data is presented as mean±standard deviation.

Example 1: Low $pO_2$ Reduces Residual mESC

We differentiated and performed extended culture on Oct4-GFP+ mESC at various $pO_2$ to reduce residual mESC. Before differentiation, greater than 95% of the mESC expressed Oct4-GFP (Oct4-GFP+) (data not shown). This fraction decreased drastically during the 10 day differentiation, and, by the start of the extended low oxygen culture, Oct4-GFP+ cells represented a small fraction ($3 \times 10^{-3}$) of the total cell population at 142 mmHg (FIG. 1A). Differentiation under 36 and 7 mmHg resulted in even greater reduction in the fraction, to $6 \times 10^{-4}$ and $1 \times 10^{-3}$, respectively. These residual Oct4-GFP+ subpopulation had GFP intensity values similar to that of undifferentiated mESC (data not shown), and we hypothesized that these cells were residual pluripotent cells that could develop into teratomas upon implantation into animals.

After differentiation, culture was extended for up to 80 additional days to further reduce the fraction of Oct4-GFP+ cells. The differentiation process was largely complete by about 10 days of culture, and we considered the subsequent days in culture to represent a teratoma reduction phase of culture. In these experiments, cells were cultured at a constant oxygen partial pressure throughout differentiation and extended culture. Extended culture at 142 mmHg did not significantly change the fraction of Oct4-GFP+ cells but at 36 and 7 mmHg resulted in a dramatic decrease in the fraction (FIG. 1A). The greatest difference was observed after 80 days of extended culture, at which point the fraction of Oct4-GFP+ cells was a factor of 1260 lower at 7 mmHg as compared to 142 mmHg. The low oxygen reduction in the fraction of Oct4-GFP in FIG. 1A can be modeled assuming first order kinetics with a rate constant of $0.102 \pm 0.006$ and $0.19950 \pm 0.00002$ day$^-$ for 36 and 7 mmHg, respectively.

Figure 1B:
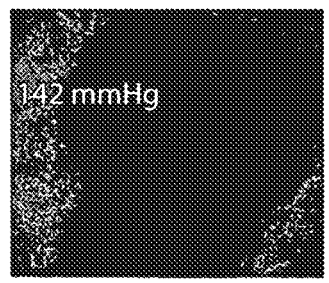
Figure 1C:
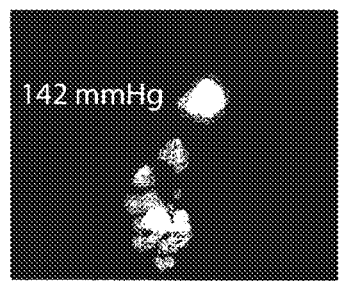
Figure 1D:
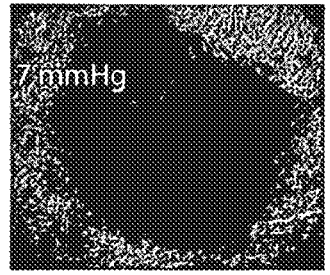
Figure 1E:
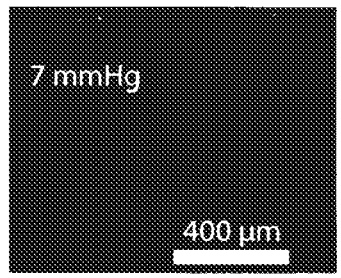

When observed with fluorescence microscopy, cells cultured at 142 mmHg that expressed GFP resided in clusters within aggregates (FIGS. 1B and 1C). However, at 7 mmHg, no cells expressing GFP were visually observed anywhere in the dish, including in aggregates (FIGS. 1D and 1E). No GFP regions were observed for cells cultured at 36 mmHg also (data not shown). The inability to visually observe Oct4-GFP+ cells at 36 or 7 mmHg with microscopy is likely due to the low fraction of cells expressing high enough levels of GFP to be detected by eye, not because of a complete absence of GFP-expressing cells.

Real-time PCR measurements demonstrated a reduction in the gene expression of Oct4 and Nanog at 36 and 7 mmHg compared to 142 mmHg (FIGS. 1F and 1G), correlating with the trend of a reduction in pluripotency at low compared to high $pO_2$.

Figure 2:
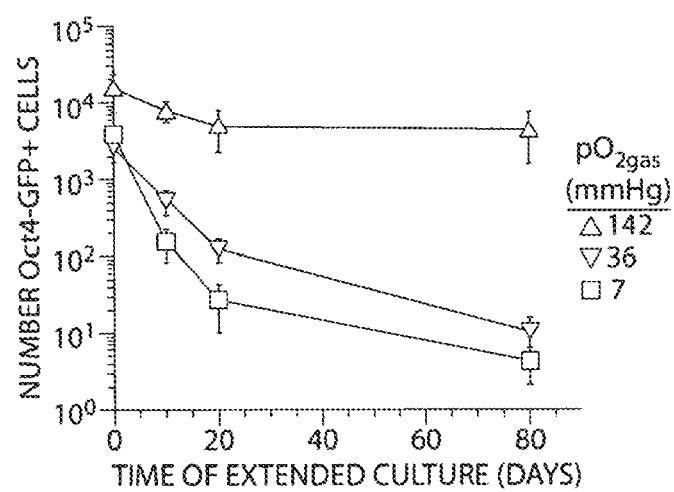
FIG. 2. The number of residual Oct4-GFP+ cells from mESC having undergone differentiation and extended culture at various $pO_{2gas}$. mESC were differentiated at 142, 36, or 7 mmHg $pO_{2gas}$ then subjected to 0, 10, 20, or 80 days of extended culture at the same $PO_{2gas}$. The number of cells that are Oct4-GFP+ was determined by multiplying the fraction of Oct4-GFP+ cells, measured with flow cytometry, and the total cell number, measured by nuclei count (n=3).

Low oxygen culture reduction the number of Oct4-GFP+ cells in addition to the fraction (FIG. 2). At the start of differentiation, each well started with $1.5 \times 10^4$ Oct4-GFP+ cells. After 10 days of differentiation at 142 mmHg, this number remained unchanged. However, after 10 days of differentiation at 36 and 7 mmHg, the number of residual Oct4-GFP+ was much lower, $3 \times 10^3$ and $4 \times 10^3$, respectively. During 20 days of extended culture, the number of Oct4-GFP+ cells decreased with culture at 142 mmHg to $5 \times 10^3$ and remained at this value until day 80. This reduction in the number of Oct4-GFP+ cells was proportional to the reduction in the total cell number (FIG. 1A). However, extended culture at 36 and 7 drastically decreased the number of Oct4-GFP+ cells, resulting in only 10 and 4 remaining Oct4-GFP+ cells per well by day 80, respectively. This reduction was substantially faster than the reduction in the total cell number, as demonstrated by the rapid decrease in the fraction of Oct4-GFP+ cells (FIG. 1A).

Example 2: Long-Term Hypoxic Culture of Differentiated mES Cells Leads to a Greatly Reduced Rate of Teratoma Formation Following Implantation in SCID Mice mES cells having undergone different $pO_{2gas}$ culture conditions and injection subcutaneously into SCID mice formed tumors at different rates. 4/4 animals injected with $10^5$ undifferentiated mES cells in Matrigel (positive control) formed visible tumors by day 14. Tumor formation was determined by visual observation of the appearance of masses underneath the skin. Differentiated cells cultured 35 extra days before implantation had slower tumor formation rates. $10^5$ mES cells were differentiated 10 days at 142 mmHg (n=4) or 36 mmHg (n=6) in Matrigel, followed by 35 days of extended culture at the same $pO_{2gas}$ to reduce the number and frequency of pluripotent cells, or only Matrigel (n=4; negative control). Visible tumors appeared in 4/4 animals after 17 days for cells cultured at 142 mmHg. Culture at lower $pO_2$ (36 mmHg) had an even greater effect. Tumors were first observed in 2/6 animals on day 31, and by day 38, 5/6 animals had developed tumors. 0/4 animals injected with only Matrigel (negative control) formed tumors. These in vivo data are consistent with the in vitro Oct4-GFP and real-time PCR data and confirm that long-term hypoxic culture of mES cells greatly reduces the rate of teratoma formation in vivo.

Figure 3A:
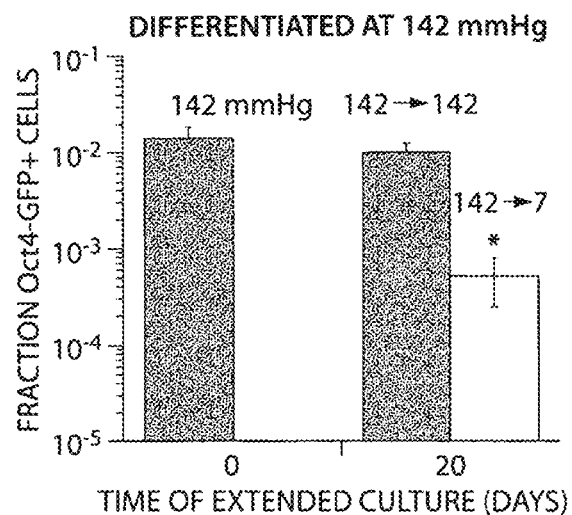
FIGS. 3A and 3B. The fraction of residual Oct4-GFP+ cells from mESC having undergone differentiation and extended culture at the same or different $pO_{2gas}$.
Figure 3B:
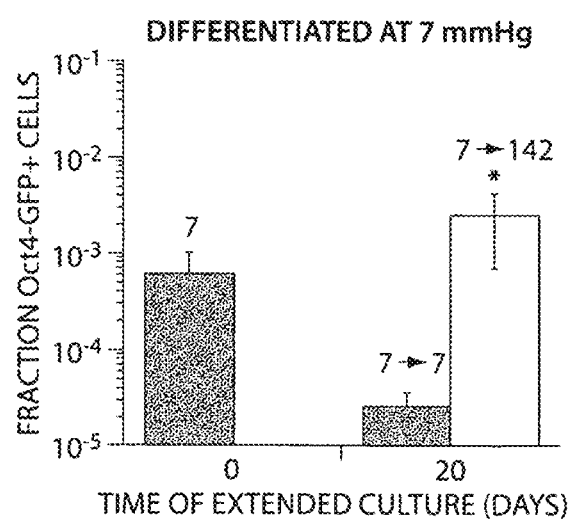

Example 3: The Effect of a Step Change in $pO_{2gas}$, on the Fraction of Oct4-GFP+ Cells To investigate the effects of using different $pO_2$ values during differentiation and extended culture on the fraction of Oct4-GFP+ cells, mESC were initially differentiated for 10 days at either 142 or 7 mmHg $pO_{2gas}$, and then subjected to 20 days extended culture at the same or the other value of $pO_{2gas}$ (FIGS. 3A and 3B). After 10 days of differentiation at 142 mmHg (FIG. 3A), the fraction of Oct4-GFP+ cells was $1.4 \times 10^{-2}$. Extended culture for 20 days at 142 mmHg did not significantly change the fraction of Oct4-GFP+ cells. However, extended culture at 7 mmHg decreased the fraction to $5 \times 10^{-4}$. 10 days of differentiation at 7 mmHg resulted in a fraction of Oct4-GFP+ cells of $6 \times 10^{-4}$, a factor of 22 lower than at 142 mmHg (FIG. 3B). Extended culture for 20 days at 7 mmHg further decreased the fraction to $3 \times 10^{-5}$. However, extended culture at 142 mmHg increased the mean fraction to $3 \times 10^{-3}$.

Example 4: Long-Term Hypoxic Culture of Differentiated mES Cells Does Not Limit Cell Survival If differentiated cells that have been previously cultured under normoxic conditions are to be cultured under hypoxic conditions in order to reduce the fraction of cells that are pluripotent, it is possible that the cells will die if they are unable to use anaerobic metabolism. To investigate this possibility, we differentiated the cells and cultured the cells for extended time with three different sequences of $pO_{2gas}$: (A) Differentiate at 142 mmHg for 10 days, then extended culture at 142 mmHg for 20 days; (B) Differentiate at 142 mmHg for 10 days, then extended culture at 7 mmHg for 20 days; (C) Differentiate at 7 mmHg for 6 days, then differentiate at 142 mmHg for 4 days, then extended culture at 7 mmHg for 20 days. With all sequences, spontaneously-contracting cells were observed. The total number of cells and the number of MF-20+ (cardiomyocyte marker) cells is tabulated in Table 3 for days 0 and 20 of extended culture, along with the relative decrease from each number from 0 to 20 days culture. At day 0 of extended culture, sequence C maximized the number and fraction of cardiomyocytes, corresponding with our previous findings. With all sequences, the total cell number and number of MF-20+ cells decreased from 0 to 20 days. The decreases were smallest with sequences B and C, which involved extended culture at 7 mmHg, compared to sequence A, which used extended culture at 142 mmHg.

Regardless of whether differentiation was carried out for the first 10 days at 142 or 7 mmHg, if the 20 day extended culture was performed at 7 mmHg, the fraction of Oct4-GFP+ cells decreased approximately by a factor of 25 compared to day 10 cells. Additionally, if the 20 day extended culture was performed at 142 mmHg, the fraction of Oct4-GFP+ cells either increased or stayed the same compared to day 0. These results demonstrate that differentiation can be performed at any $pO_2$, followed by an extended culture period at low $pO_2$ to reduce the fraction of Oct4-GFP+ cells without negative affecting cell number. This combination of $pO_2$ control strategies allows for the production of the desired differentiated cell type at the best $pO_2$ for producing that cell type while also reducing the fraction of potentially-tumorigenic residual pluripotent cells.

Example 5: Low $pO_2$ Delays Appearance of Tumors after Implantation of Cultured mESC mESC having undergone different $pO_{2gas}$ culture conditions and injection subcutaneously into nude mice formed tumors at different rates (FIG. 4A). 6/6 animals injected with undifferentiated mESC (positive control) formed visible tumors by day 14. Differentiated cells cultured 20 extra days before implantation had slower tumor formation rates. Visible tumors appeared in 7/8 animals by day 17 and 8/8 by day 21 for cells cultured at 142 mmHg. Culture at lower $pO_2$ (36 and 7 mmHg) had an even greater effect. Tumors were first observed in 3/8 animals by day 31, 5/8 by day 35, and 7/8 by day 38 for cells cultured at 36 mmHg and in 5/8 animals by day 35, 6/8 animals by day 38, and 7/8 animals by day 42 for 7 mmHg. 0/6 animals injected with only Matrigel (negative control) formed tumors. All animals with no tumors were monitored for a total of 210 days after implantation, during which no tumors were observed.

Figure 4A:
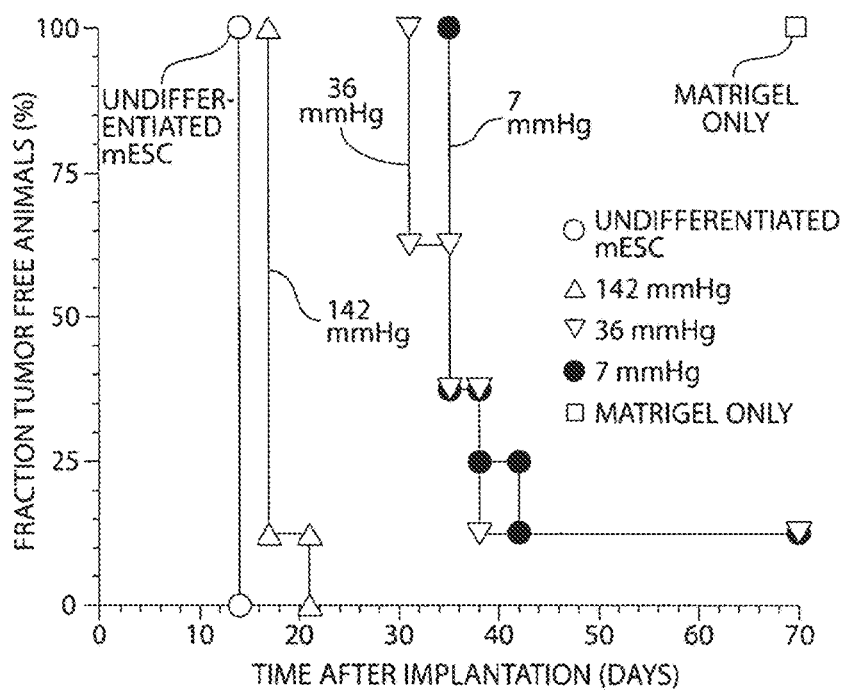
FIGS. 4A and 4B. Time-course development of tumors in nude mice after subcutaneous implantation of mESC.
Figure 4B:
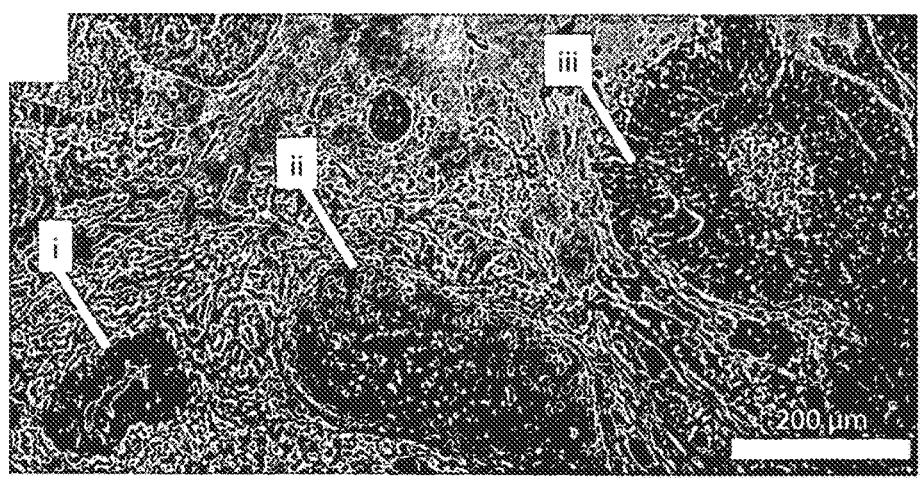

The resulting tumors were excised from sacrificed mice, fixed, embedded, sectioned, and H&E stained, and the resulting tissue sections histopathologically analyzed (FIG. 4B). The tumors contained derivatives of all three germ layers and were identified as teratomas. These in vivo data are consistent with the in vitro Oct4-GFP and real-time PCR data and confirm that long-term hypoxic culture of mESC greatly reduces the rate of teratoma formation in vivo.

Figure 5A:
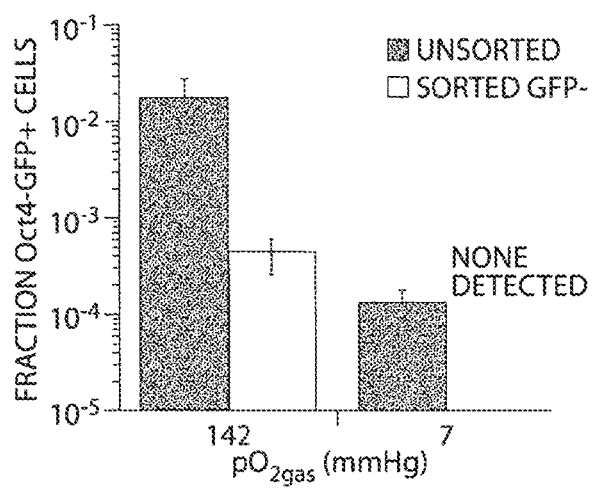
FIGS. 5A to 5C. Expression of Oct4-GFP and time-course development of tumors in nude mice after subcutaneous implantation of mESC sorted into GFP+ and GFP− populations. mESC were differentiated and cultured 20 extra days at either 142 or 7 mmHg $pO_{2gas}$.
Figure 5B:
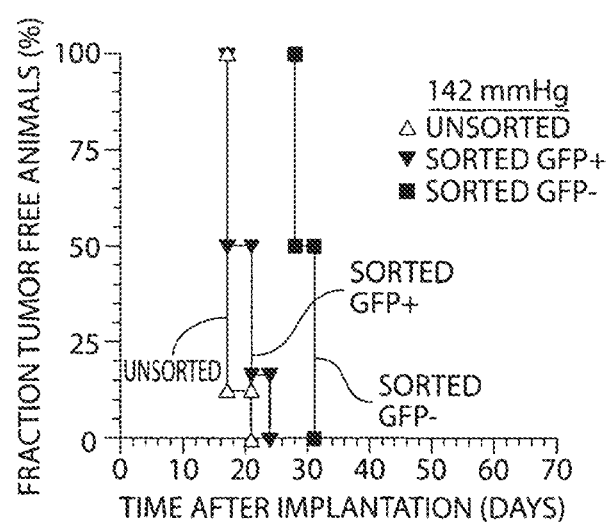

Example 6: Combination of Low $pO_2$ Culture with Fluorescence Activated Cell Sorting (FACS)

mESC after differentiation and 20 days of extended culture were sorted with FACS based on GFP expression into Oct4-GFP− and Oct4-GFP+ populations before implantation to investigate Oct4-GFP+ cells as the tumor cell source (FIGS. 5A and 5B). FACS was unable to remove all the Oct4-GFP+ cells from the 142 mmHg Oct4-GFP− population, instead decreasing the fraction of Oct4-GFP+ cells by a factor of 50, as determined by subsequent flow cytometric analysis of the sorted population, but was able to remove all Oct4-GFP+ cells from the 7 mmHg Oct4-GFP+ population (FIG. 5A). After FACS, unsorted, Oct4-GFP+ populations, and the Oct4-GFP− populations from 142 and 7 mmHg were implanted into nude mice (FIG. 5B). The 142 and 7 mmHg Oct4-GFP+ populations resulted in tumors that appeared at approximately the same time as 142 and 7 mmHg unsorted cells, respectively. The 142 mmHg Oct4-GFP− population resulted in an 11 day delay in tumor appearance compared to unsorted cells, but the 7 mmHg Oct4-GFP− population resulted in no tumors during 210 days of observation. The complete absence of tumor formation with Oct4-GFP− populations verified to contain no Oct4-GFP− cells demonstrates that only Oct4-GFP+ pluripotent stem cells are responsible for the tumor formation in this system, confirming our approach of focusing on this subpopulation.

Figure 5C:
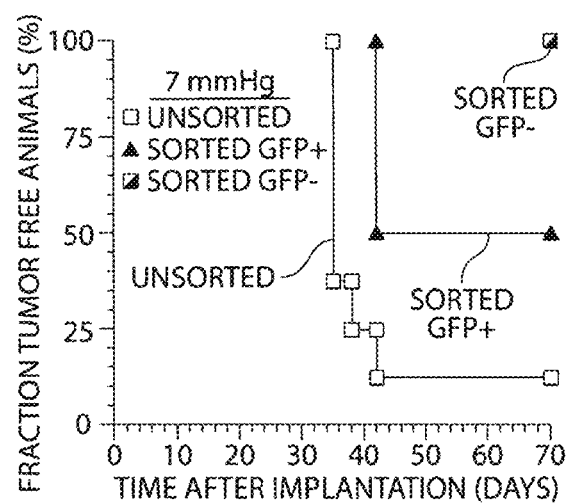
Figure 6A:
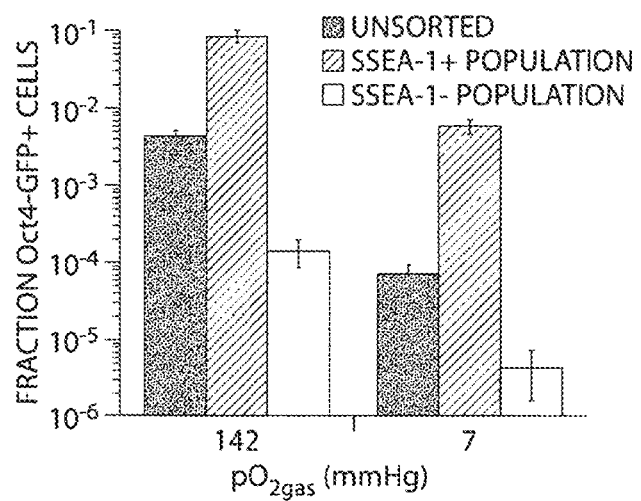
FIGS. 6A and 6B. Expression of pluripotency markers and time-course development of tumors in nude mice after subcutaneous implantation of mESC differentiated 10 days followed by 20 days extended culture at 142 or 7 mmHg $pO_{2gas}$, then sorted into SSEA-1+ and SSEA-1− populations.
Figure 6B:
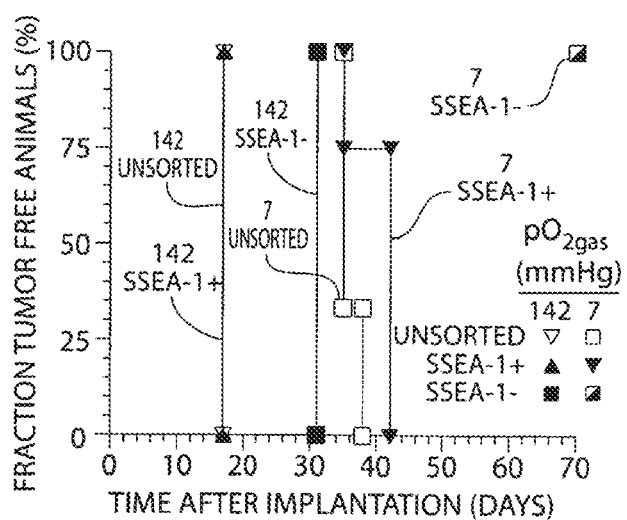

The data in FIGS. 5A to 5C also shows that low $pO_2$ culture can be combined with FACS to further decrease and eliminate residual pluripotent cells. However, sorting based on GFP expression requires cells containing genetic modifications, which creates another major hurdle to clinical application. Therefore, we investigated combining low $pO_2$ culture with sorting based on staining with a PE-conjugated anti-SSEA-1 antibody (FIGS. 6A and 6B). mESC, after differentiation and 20 days of extended culture, were sorted into SSEA-1+ and SSEA-1− populations and subsequently analyzed with flow cytometry for Oct4-GFP expression (FIG. 6A). The SSEA-1− populations had a fraction of Oct4-GFP+ cells that were a factor of 31 and 16 lower than unsorted cells from 142 and 7 mmHg, respectively. Culture at 7 mmHg combined with FACS removal of SSEA-1+ cells resulted in a reduction in the fraction of Oct4-GFP+ cells by a factor of 1020 compared to cells culture at 142 mmHg without sorting. After FACS, unsorted, SSEA-1+ populations, and the SSEA-1− populations from 142 and 7 mmHg were implanted into nude mice (FIG. 6B). The 142 and 7 mmHg SSEA-1+ populations resulted in tumors that appeared at approximately the same time as 142 and 7 mmHg unsorted cells, respectively. The 142 mmHg SSEA-1− population resulted in a 14-day delay in tumor appearance compared to unsorted cells, but the 7 mmHg SSEA-1− population resulted in no tumors during 210 days of observation. Low $pO_2$ culture can be used in combination with FACS removal based on surface markers to eliminate the risk of tumor formation.

Figure 1F:
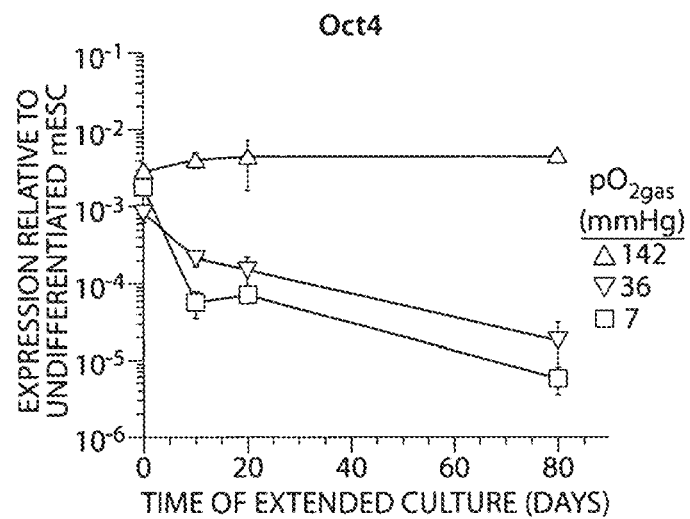
Figure 1G:
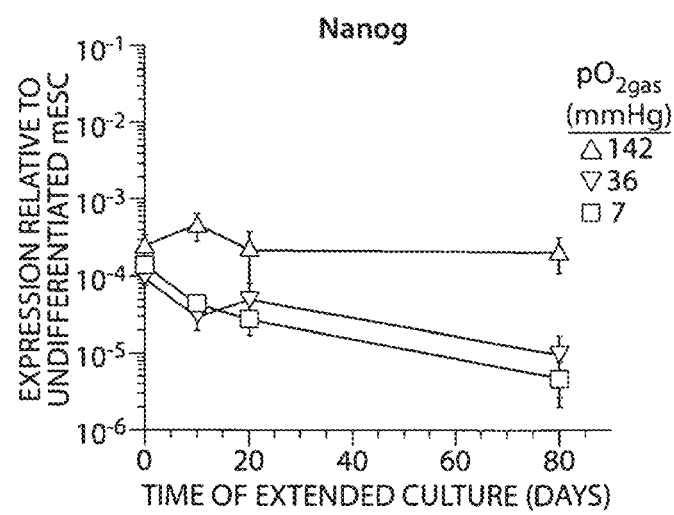
Figure 7A:
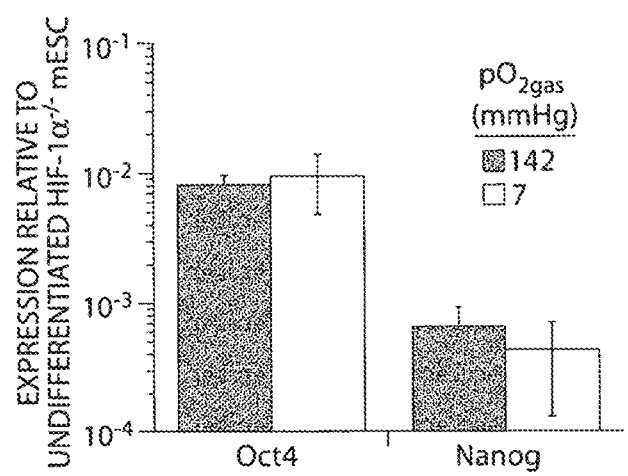
FIGS. 7A and 7B. Expression of pluripotency markers and time-course development of tumors in nude mice after subcutaneous implantation of HIF-1α$^{-/-}$ mESC cells differentiated 10 days, followed by 20 days extended culture at 142 or 7 mmHg $pO_{2gas}$.
Figure 7B:
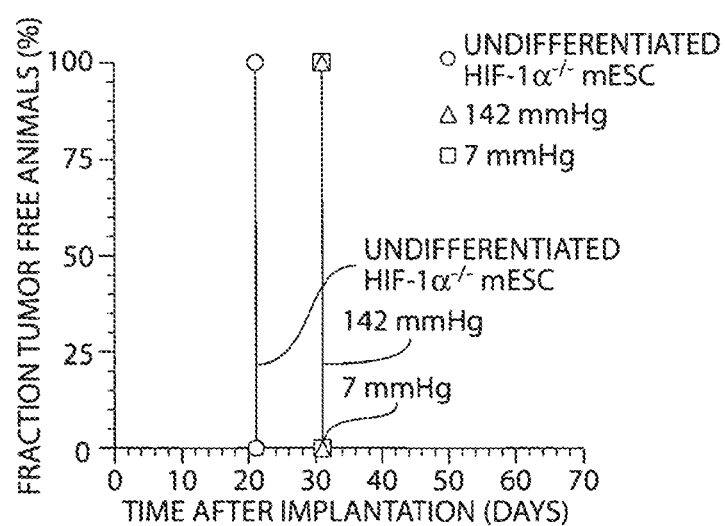

Example 7: HIF-1α is Necessary for the Low $pO_2$ Reduction in Residual mESC and Delay in Appearance of Tumors after Implantation of Cultured mESC To determine if HIF-1α is necessary for the low $pO_2$ reduction in residual mESC and delay in appearance of tumors after implantation of cultured mESC, a HIF-1α$^{-/-}$ mESC line was differentiated and subjected to extended culture (FIGS. 7A and 7B). After 20 days of extended culture, Oct4 and Nanog gene expression was the same between 142 and 7 mmHg (FIG. 7A). The relative loss of Oct4 and Nanog gene expression for HIF-1α$^{-/-}$ mESC at both pO$_{2gas}$ conditions was similar to the relative loss of expression of wild type mESC at 142 mmHg (FIGS. 1F and 1G). Upon implantation into nude mice, all animals injected with undifferentiated HIF-1α$^{-/-}$ mESC formed tumors by day 21, 7 days later than wild type mESC (FIG. 4A). Differentiated HIF-1α$^{-/-}$ mESC cultured 20 extra days before implantation had slower tumor formation rates, with all animals forming tumors by day 31, regardless of culture pO$_{2gas}$ (7 or 142 mmHg), 14 days later than wild type mESC cultured at 142 mmHg. Without HIF-1α, pluripotency gene expression and tumor formation rates are the same between low and high pO$_2$, showing that HIF-1α is necessary for the positive benefits of low pO$_2$ culture.

Example 8: Residual Oct4-GFP+ mESC In Vitro Phenotype is the Same as Undifferentiated mESC Oct4-GFP+ cells separated from Oct4-GFP− cells after 10 days of differentiation and 35 days of extended culture at 7 mmHg were plated onto gelatin-coated polystyrene in DMEM with 10% FBS and 10$^3$ U/ml LIF (data not shown). The Oct4-GFP+ cells proliferated once separated from Oct4-GFP− cells. Their morphology resembled that of undifferentiated ES cells.

Figure 8A:
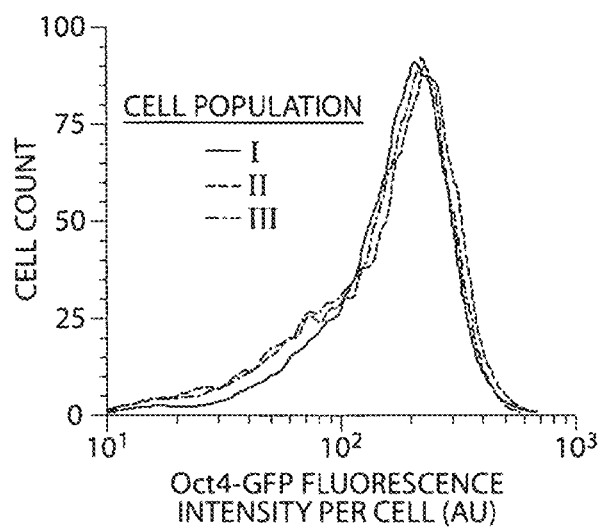
FIGS. 8A to 8F. Characterization of (I) Oct4-GFP+ mESC that have never undergone differentiation and extended culture, (II) Oct4-GFP+ cells sorted with FACS from mESC that have undergone 10 days differentiation and 20 days extended culture at 142 mmHg, and (III) Oct4-GFP+ cells cultured similar to case II, but at 7 mmHg.
Figure 8B:
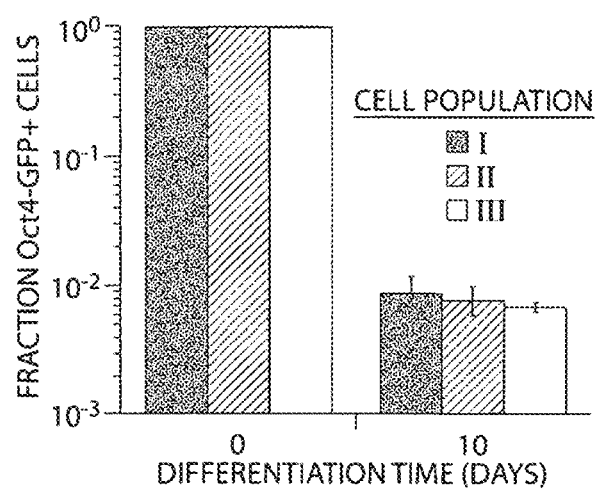
Figure 8C:
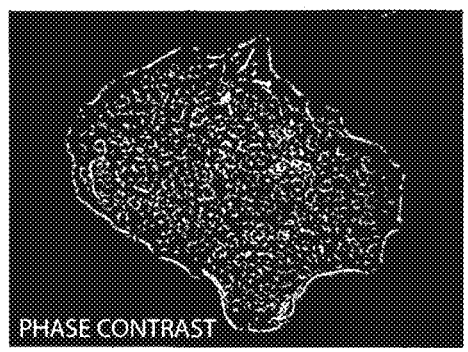
Figure 8D:
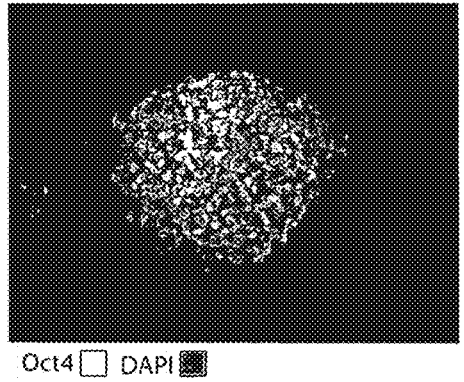
Figure 8E:
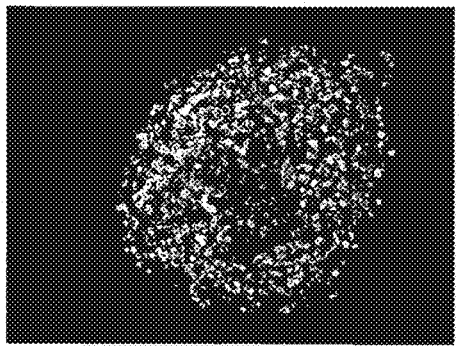
Figure 8F:
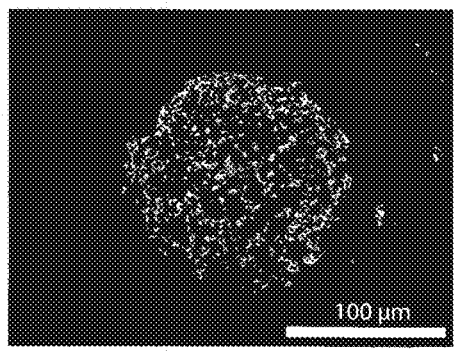
Figure 9A:
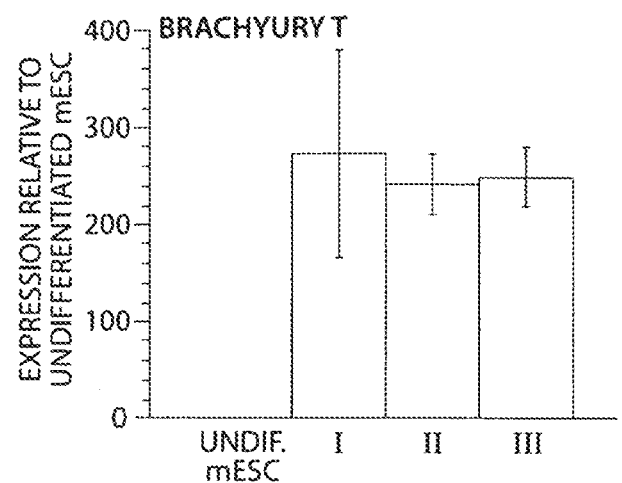
FIGS. 9A to 9F. Differentiation of cases I, II, and III and assessment with real-time PCR. Expression of FIG. 9A: Brachyury T.
Figure 9B:
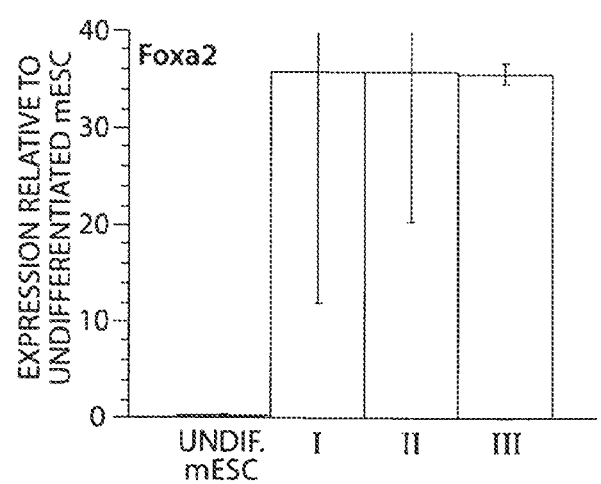
Figure 9C:
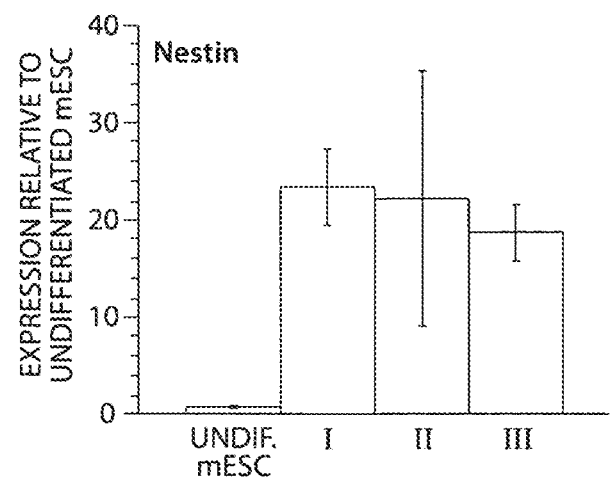
Figure 9D:
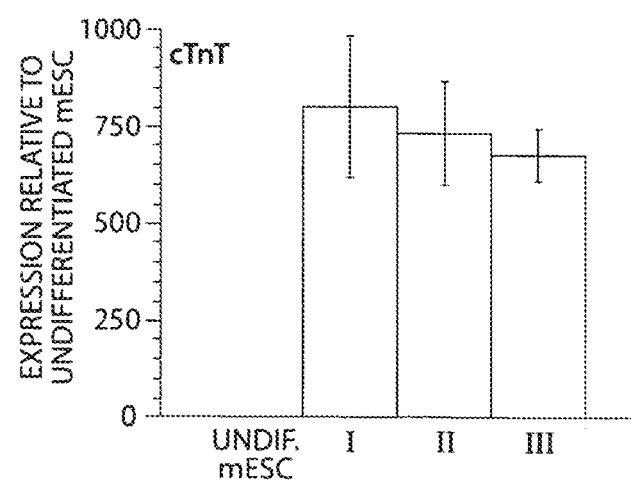
Figure 9E:
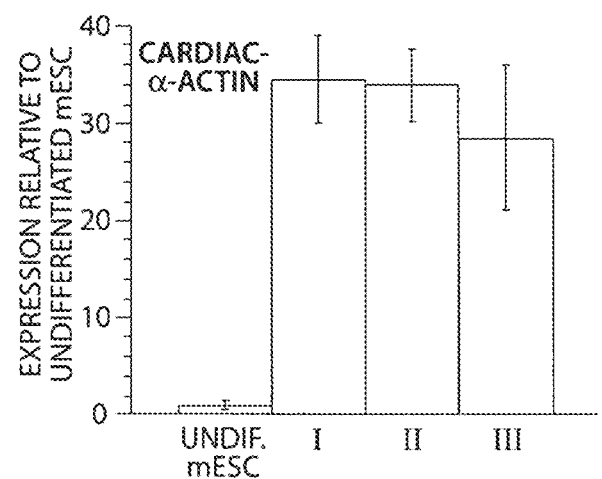
Figure 9F:
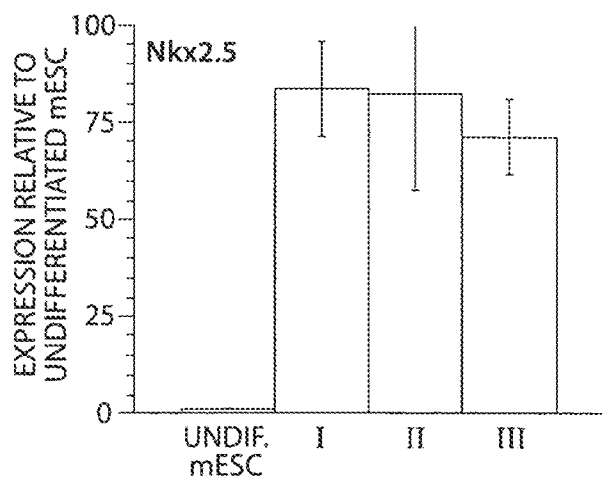
Figure 10A:
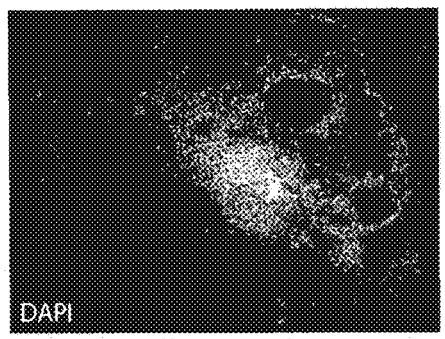
FIGS. 10A to 10F. Differentiation of cases I, II, and III and assessment with immunocytochemistry. En face images cells after
Figure 10B:
Figure 10C:
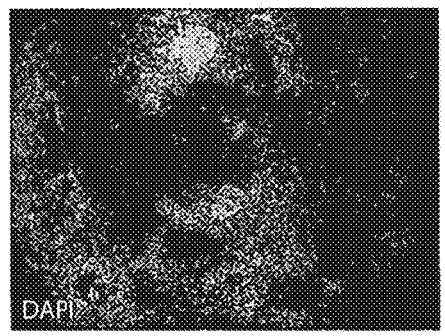
Figure 10D:
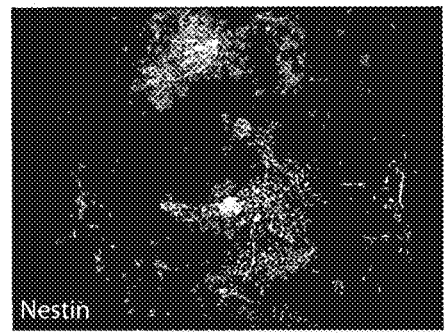
Figure 10E:
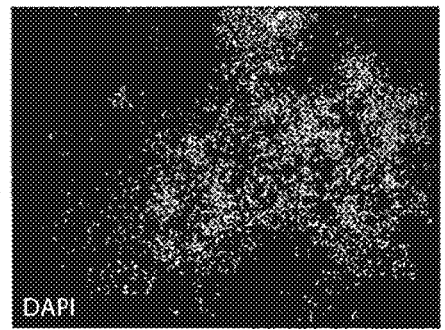
Figure 10F:
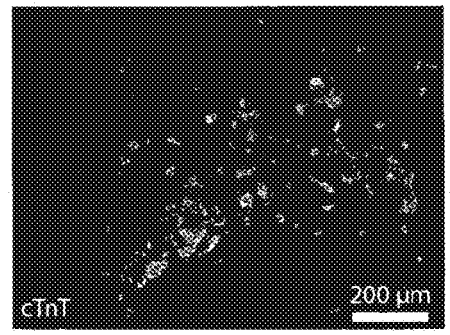
Figure 11A:
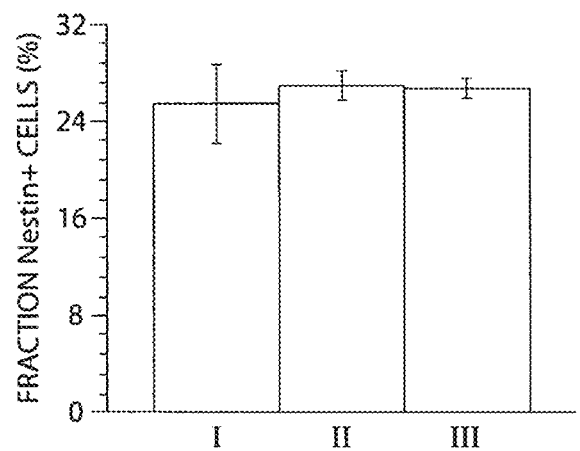
FIGS. 11A to 11D. Differentiation of cases I, II, and III and assessment with flow cytometry.
Figure 11B:
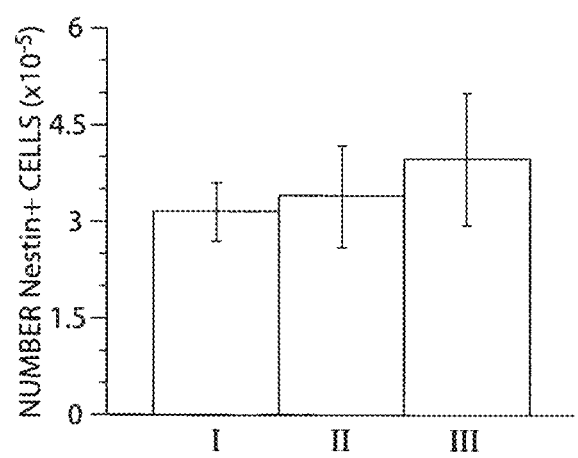
Figure 11C:
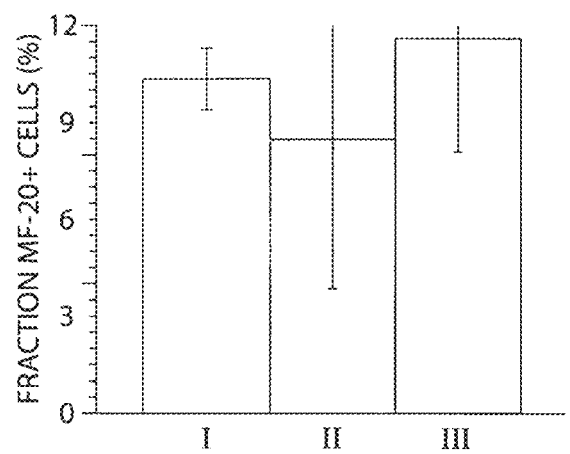
Figure 11D:
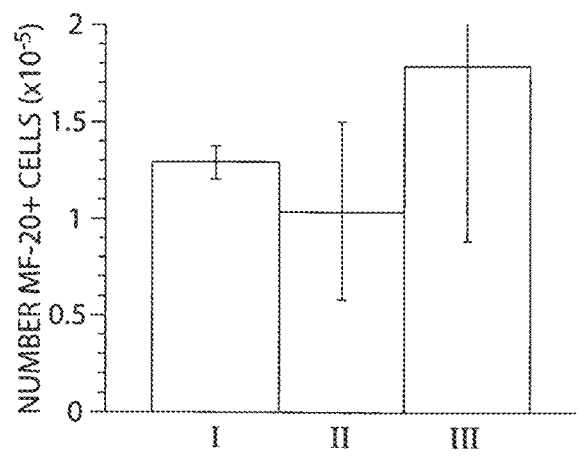

We further investigated residual Oct4-GFP+ mESC by removing Oct4-GFP+ cells from differentiated mixtures, plating them in LIF-supplemented media, and characterizing their in vitro phenotype. Specifically, we compared three cases: (I) Oct4-GFP+ mESC that have never undergone differentiation and extended culture, (II) Oct4-GFP+ mESC sorted with FACS from mESC that have undergone differentiation and 20 days extended culture at 142 mmHg, and (III) Oct4-GFP+ mESC cultured similar to case II, but at 7 mmHg (FIGS. 8-11). The distribution of Oct4-GFP intensity was similar among the three cases (FIG. 8A), and Oct4-GFP expression was lost in greater than 99% of resulting cells when differentiated (FIG. 8B). Oct4-GFP+ mESC colonies among all three cases were morphologically similar and contained Oct4, Nanog, and SSEA-1 protein (FIG. 8C to 8F). Upon differentiation, all three cases expressed markers for all three germ layers (FIGS. 9-11). All three cases (1) expressed Brachyury T, Foxa2, Nestin, cardiac Troponin T (cTnT), cardiac-α-Actin, and Nkx2.5 mRNA (FIGS. 9A to 9F), (2) stained positive for Foxa2, Nestin, and cTnT protein (FIGS. 10A to 10F), and (3) contained the same fraction and number of Nestin+ and MF-20+ cells (FIGS. 11A to 11F). According to all the in vitro characterization assays we formed, residual Oct4-GFP+ mESC are the same as undifferentiated mESC.

Figure 12A:
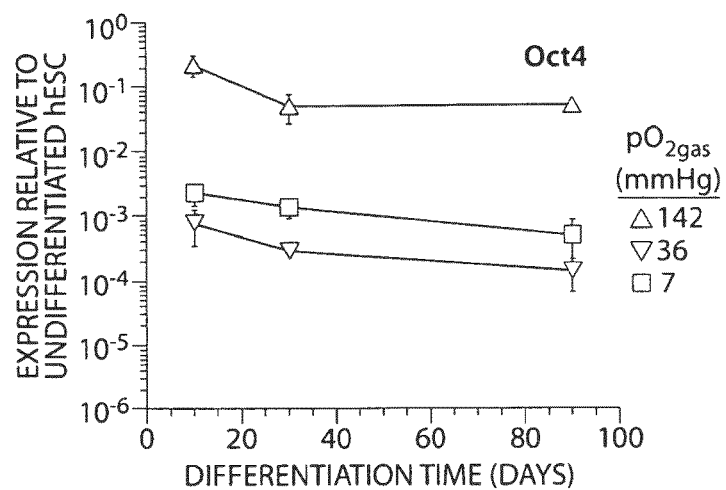
FIGS. 12A to 12C. Expression of pluripotency markers and time-course development of tumors from hESC having undergone differentiation at various $pO_{2gas}$. hESC were differentiated at 142, 36, or 7 mmHg $pO_{2gas}$ up to 90 days.
Figure 12B:
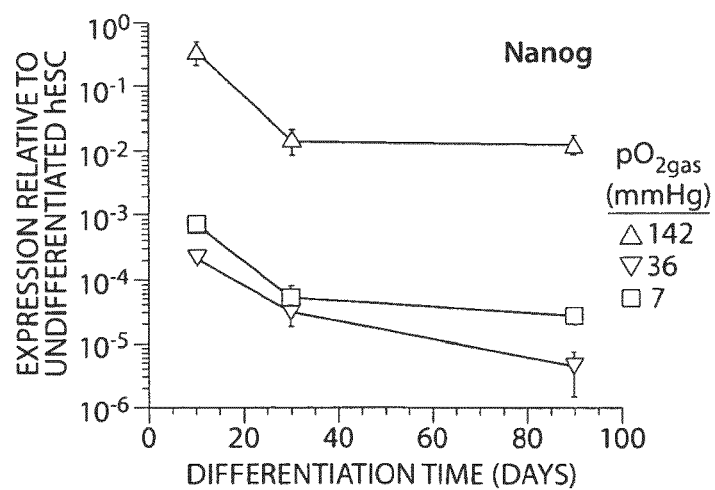
Figure 12C:
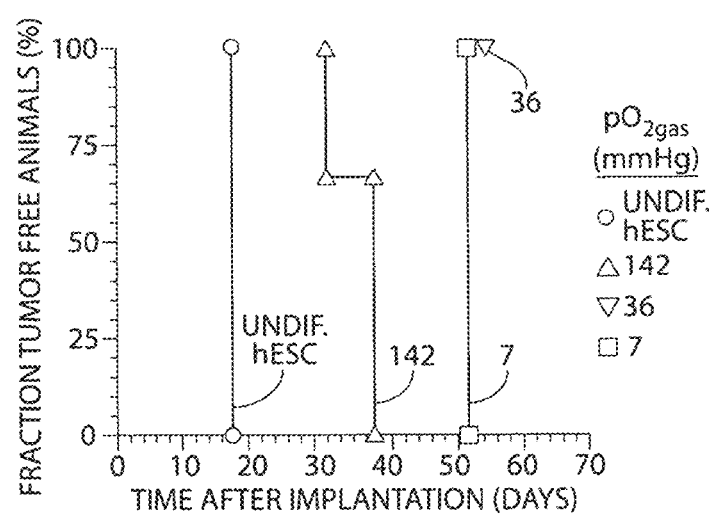

Example 9: Low pO$_2$ Reduces in Residual hESC and Delays the Appearance of Tumors after Implantation of Cultured Hesc We extended our investigation to hESC by differentiating CyT49 hESC at various pO$_2$ to reduce residual hESC (FIGS. 12A to 12C). Before differentiation, more than 95% of the hESC stained positive for OCT4 protein (data not shown). During differentiation, OCT4 and NANOG gene expression decreased drastically and was lowest under low pO$_2$ (FIGS. 12A and 12B). For culture at 142 mmHg, OCT4 and NANOG gene expression decreased until day 30, then remained constant until day 90. For culture at 36 and 7 mmHg, expression decreased during the entire 90 day period and was lower at all time points compared to 142 mmHg. After 90 days of differentiation, OCT4 expression was 357 and 102 times lower at 36 and 7 mmHg, respectively, and NANOG expression was 2844 and 456 times lower at 36 and 7 mmHg, respectively, compared to 142 mmHg. These results are qualitatively similar to data with mESC, but the loss of expression compared to undifferentiated cells is lower in hESC compared to mESC (FIGS. 1F and 1G). These in vitro results demonstrate that differentiation under low pO$_2$ can reduce pluripotency gene expression.

hESC having undergone 30 days of differentiation at different pO$_{2gas}$ culture conditions and injection subcutaneously into nude mice formed tumors at different rates (FIG. 12C). All animals injected with undifferentiated hESC (positive control) formed visible tumors by day 17. Cells differentiated 30 days before implantation had slower tumor formation rates. Visible tumors appeared in 2/6 animals by day 31 and 6/6 by day 38 for cells cultured at 142 mmHg. Culture at lower pO$_2$ (36 and 7 mmHg) had an even greater effect. Tumors were observed in all animals by day 52 for cells cultured at 7 mmHg. As of day 55, no animals with cells from 36 mmHg have formed tumors. These in vivo data are consistent with the in vitro real-time PCR data and confirm that hypoxic culture of hESC greatly reduces the rate of teratoma formation in vivo.

Example 10: Low pO$_2$ Reduces Residual miPSC

Figure 13:
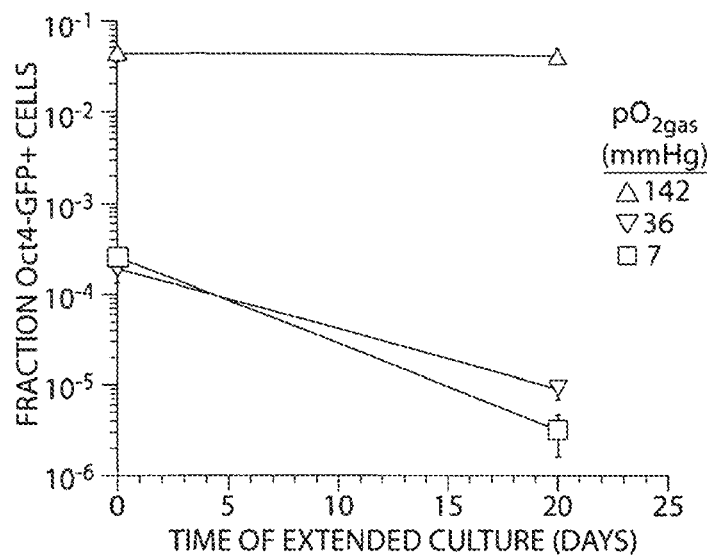
FIG. 13. The fraction of residual Oct4-GFP+ cells from miPSC having undergone differentiation and extended culture at various $pO_{2gas}$. mESC were differentiated at 142, 36, or 7 mmHg $pO_{2gas}$ then subjected to 0 or 20 days of extended culture at the same $pO_{2gas}$. The fraction of Oct4-GFP+ cells was acquired with flow cytometry (n=3).

We extended our investigation to miPSC by differentiating Oct4-GFP+ miPSC at various pO$_2$ to reduce residual miPSC (FIG. 13). Before differentiation, greater than 95% of the miPSC were Oct4-GFP+ (data not shown). This fraction decreased drastically during the 10 day differentiation, and, by the start of the extended low oxygen culture, Oct4-GFP+ cells represented a small fraction (4×10$^{-2}$) of the total cell population at 142 mmHg. Differentiation under 36 and 7 mmHg resulted in even greater reduction in the fraction, to 2×10$^{-4}$ and 3×10$^{-4}$, respectively. These residual Oct4-GFP+ subpopulation had GFP intensity values similar to that of undifferentiated miPSC (data not shown). After differentiation, culture was extended for 20 additional days to further reduce the fraction of Oct4-GFP+ cells. Extended culture at 142 mmHg did not significantly change the fraction of Oct4-GFP+ cells but at 36 and 7 mmHg resulted in a dramatic decrease in the fractions. The greatest difference was observed after 20 days of extended culture, at which point the fraction of Oct4-GFP+ cells was a factor of 13203 lower at 7 mmHg compared to 142 mmHg. These results are qualitatively similar to data with mESC, but the loss of expression compared to undifferentiated cells is higher at low pO$_2$ and lower at high pO$_2$ in miPSC compared to mESC (FIG. 1A). These in vitro results demonstrate that differentiation and extended culture under low pO$_2$ can reduce residual miPSC.

Figure 14:
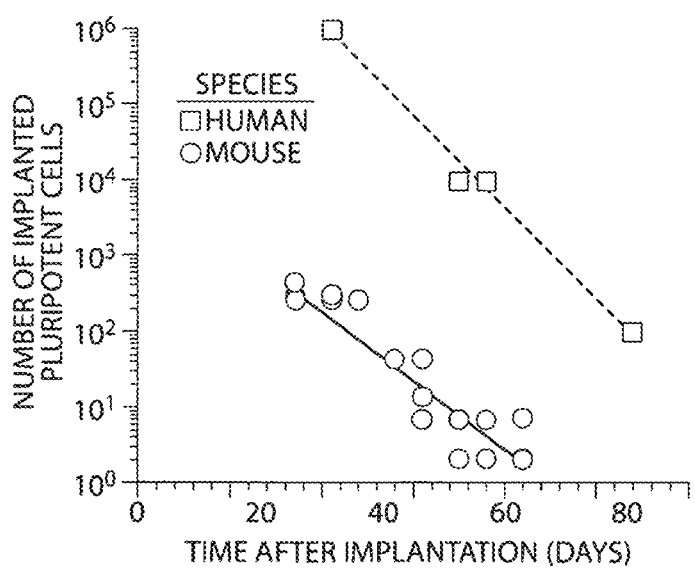
FIG. 14. The time required for tumor appearance after implantation of different numbers mESC and hESC. The number of implanted residual Oct4-GFP mESC, having undergone differentiation and extended culture under various conditions (FIGS. 1A, 4A, and 5A), is plotted against the corresponding tumor formation data (FIGS. 3A, 4B, 4C, and 5B) (circles; n=68). $10^6$, $10^4$, and $10^2$ undifferentiated hESC were implanted and the appearance of tumors observed (squares; n=6). The mouse (solid line) and human (dashed line) data fit the form $y=Ae^{Bx}$, where $A=1.22 \times 10^4$ and $3.03 \times 10^8$ and $B=-0.209$ and $-0.278$, respectively.

Example 11: Number of Implanted Pluripotent Cells Correlates with the Appearance of Tumors To better assess our nude mouse model for detecting residual pluripotent cells, we compared the number of implanted Oct4-GFP+ mESC and hESC to the time required to form a tumor (FIG. 14). The mouse and human data correlated and fit an exponential equation, with $R^2=0.90$ and $R^2=0.99$, respectively. Undifferentiated mESC data was not included, because we observed that implanting $10^5$ and $10^6$ undifferentiated mESC both formed tumors on day 14, suggesting there is an upper limit on the sensitivity of this animal model. This data shows that our animal model is very sensitive to small numbers of and could be used in the estimation of residual pluripotent cells.

REFERENCES CITED

1. Zhou, Q., H. Chipperfield, D. A. Melton, and W. H. Wong, *A gene regulatory network in mouse embryonic stem cells*. Proc Natl Acad Sci USA, 2007. 104(42): p. 16438-43.
2. Brusselmans, K., F. Bono, D. Collen, J. M. Herbert, P. Carmeliet, and M. Dewerchin, *A novel role for vascular endothelial growth factor as an autocrine survival factor for embryonic stem cells during hypoxia*. J Biol Chem, 2005. 280(5): p. 3493-9.
3. Powers, D. E., J. R. Millman, S. Bonner-Weir, M. J. Rappel, and C. K. Colton, *Accurate control of oxygen level in cells during culture on silicone rubber membranes with application to stem cell differentiation*. Biotechnol Prog, 2009.
4. Powers, D. E., J. R. Millman, R. B. Huang, and C. K. Colton, *Effects of oxygen on mouse embryonic stem cell growth, phenotype retention, and cellular energetics*. Biotechnol Bioeng, 2008. 101(2): p. 241-54.
5. Lawrenz, B., H. Schiller, E. Willbold, M. Ruediger, A. Muhs, and S. Esser, *Highly sensitive biosafety model for stem-cell-derived grafts*. Cytotherapy, 2004. 6(3): p. 212-22.

TABLE 1

Composition of undifferentiated mES cell maintenance and mES cell differentiation medium[a]

| Component | Manufacturer and Catalogue Number | Volume per liter of medium (ml) | Notes |
|---|---|---|---|
| Dulbecco's modified eagles medium (DMEM) | ATCC SCRR 2010 | 868 | ES cell qualified |
| Fetal bovine serum | ATCC SCRR 30-2020 | 100 | ES cell qualified |
| L-alanyl-L-glutamine | ATCC SCRR 20-2115 | 10 | 200 mM stock solution |
| MEM non-essential amino acid solution | ATCC SCRR 20-2116 | 10 | |
| 2-mercaptoethanol solution | Sigma-Aldrich M7522 | 10 | 10 mM stock solution prepared in DMEM |
| Leukemia inhibitory factor[a] | Chemicon ESG 1106 | 1 | $10^6$ unit/ml stock solution |

[a]Leukemia inhibitory factor was added only to undifferentiated ES cell maintenance medium. Ascorbic acid was added only to ES cell differentiation medium.

TABLE 2

Formulation of serum-free medium

| Component | Manufacturer and Catalogue Number | Volume per liter of medium (ml) | Notes |
|---|---|---|---|
| Dulbecco's modified eagles medium (DMEM) | Mediatech 90-133-PB | 485 | 8.4 mg/ml stock solution prepared in deionized water |
| Sodium bicarbonate | Mediatech 25-035-CI | 10 | 7.5% (w/v) solution |
| F12 nutrient mixture | Invitrogen 31765-035 | 496 | |
| 25M glucose solution | Sigma-Aldrich G8769 | 1.6 | Final medium concentration of 9 mM |
| Human insulin solution | Sigma-Aldrich I9278 | 0.5 | 10 mg/ml solution |
| Holo transferrin solution | Sigma-Aldrich T1283 | 5 | 10 mg/ml stock solution prepared in DPBS |
| Sodium selenite solution | Sigma-Aldrich S9133 | 0.26 | 0.12 mM stock solution prepared in DPBS |

TABLE 3

Comparison of changes in $pO_{2gas}$ on total cell number and number of MF-20+ cells

| | | Total cell number ($\times 10^6$) | | | Number MF-20+ cells ($\times 10^5$) | | |
|---|---|---|---|---|---|---|---|
| | | Time (days)[a] | | | Time (days)[a] | | |
| $pO_{2gas}$ (mmHg) | Ascorbic Acid | 0 | 20 | Change (%) | 0 | 20 | Change (%) |
| 142 | No | 1.8 ± 0.1 | 0.7 ± 0.2 | 63 | 1.4 ± 0.1 | 0.5 ± 0.01 | 66 |
| 142-7[b] | No | 1.8 ± 0.1 | 0.9 ± 0.1 | 50 | 1.4 ± 0.1 | 1.2 ± 0.1 | 17 |
| 7-142-7[c] | Yes | 2.1 ± 0.4 | 1.0 ± 0.2 | 54 | 3.2 ± 0.3 | 2.6 ± 0.6 | 19 |

[a]Time in extended culture
[b]Differentiation 10 d at 142 mmHg, then 20 d extended culture at 7 mmHg
[c]Differentiation 6 d at 7 mmHg followed by 4 d at 142 mmHg, then 20 d extended culture at 7 mmHg

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for reducing residual pluripotent stem cells in an in vitro differentiated cell population, comprising
culturing an in vitro differentiated cell population at an oxygen partial pressure that is less than 142 mmHg for at least 1 day and less than 10 days, and
harvesting the differentiated cell population after the culturing step;
wherein the harvested cell population comprises less than 1 pluripotent stem cell per $10^3$ cells,
wherein 50% or more of the cells in the in vitro differentiated cell population are positive for at least one differentiation marker before the culturing step.

2. The method of claim 1, wherein the in vitro differentiated cell population comprises non-cardiomyocyte lineage cells.

3. The method of claim 1, wherein the in vitro differentiated cell population comprises pancreatic islet cells.

4. The method of claim 1, wherein the in vitro differentiated cell population is cultured for 1 day, 2 days, 3 days, 4 days, 5 days, 6 days, 7 days, 8 days or 9 days.

5. The method of claim 1, wherein the in vitro differentiated cell population is derived from in vitro differentiation of an embryonic stem cell or an induced pluripotent stem cell.

6. The method of claim 1, wherein the oxygen partial pressure is less than 140 mmHg, less than 120 mmHg, less than 100 mmHg, less than 80 mmHg, less than 70 mmHg, less than 60 mmHg, less than 50 mmHg, 40 less than 40 mmHg, less than 30 mmHg, less than 20 mmHg, less than 10 mmHg or lower.

7. The method of claim 1, wherein the oxygen partial pressure is in the range of 100-140 mmHg.

8. The method of claim 1, wherein the oxygen partial pressure is in the range of 50-100 mmHg.

9. The method of claim 1, wherein the oxygen partial pressure is in the range of 10-50 mmHg.

10. The method of claim 1, wherein the oxygen partial pressure is in the range of 4-10 mmHg.

11. The method of claim 1, wherein the in vitro differentiated cell population is cultured in a culture vessel comprising an oxygen permeable membrane.

12. The method of claim 1, wherein the in vitro differentiated cell population is cultured in a culture vessel comprising a silicon rubber membrane.

13. The method of claim 1, further comprising measuring the residual pluripotent stem cells in the cultured differentiated cell population.

14. A differentiated cell population obtained according to the method of claim 1.

15. A method for reducing residual pluripotent stem cells in an in vitro differentiated cell population, comprising
culturing an in vitro differentiated cell population at an oxygen partial pressure that is less than 142 mmHg for at least 1 day and less than 10 days to reduce the pluripotent stem cell number to less than 1 pluripotent stem cell per $10^5$ cells, and
harvesting the differentiated cell population after the culturing step.

16. A method for reducing residual pluripotent stem cells in an in vitro differentiated cell population, comprising
differentiating a population of pluripotent stem cells into an in vitro differentiated cell population under normoxic conditions,
culturing the in vitro differentiated cell population at an oxygen partial pressure that is less than 142 mmHg for at least 1 day and less than 10 days, and
harvesting the differentiated cell population after the culturing step;
wherein the harvested cell population comprises less than 1 pluripotent stem cell per $10^3$ cells.

17. The method of claim 16, wherein 50% or more of the cells in the in vitro differentiated cell population are positive for at least one differentiation marker before the culturing step.

* * * * *